(12) United States Patent
LaVoie et al.

(10) Patent No.: US 7,319,105 B2
(45) Date of Patent: *Jan. 15, 2008

(54) CYTOTOXIC AGENTS

(75) Inventors: Edmond J. LaVoie, Princeton Junction, NJ (US); Alexander L. Ruchelman, Robbinsville, NJ (US); Sudhir K. Singh, Bangalore (IN); Abhijit Ray, Orissa (IN); Leroy F. Liu, Bridgewater, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/846,936

(22) Filed: May 14, 2004

(65) Prior Publication Data

US 2005/0009825 A1    Jan. 13, 2005

Related U.S. Application Data

(63) Continuation of application No. PCT/US02/36604, filed on Nov. 14, 2002.

(60) Provisional application No. 60/333,051, filed on Nov. 14, 2001, provisional application No. 60/333,040, filed on Nov. 14, 2001, provisional application No. 60/332,970, filed on Nov. 14, 2001, provisional application No. 60/332,733, filed on Nov. 14, 2001, provisional application No. 60/332,698, filed on Nov. 14, 2001.

(51) Int. Cl.
| | |
|---|---|
| C07D 491/22 | (2006.01) |
| A61K 31/4741 | (2006.01) |
| A61K 31/4355 | (2006.01) |
| A61P 35/00 | (2006.01) |
| C07D 491/147 | (2006.01) |
| C07D 491/153 | (2006.01) |
| C07D 237/26 | (2006.01) |
| A61K 31/5025 | (2006.01) |

(52) U.S. Cl. ............... 514/280; 546/48; 546/41; 546/44; 546/49; 544/233; 544/238; 544/342; 514/248; 514/249

(58) Field of Classification Search ............... 546/48, 546/41, 44, 49; 514/280
See application file for complete search history.

(56) References Cited

U.S. PATENT DOCUMENTS

| | | | |
|---|---|---|---|
| 2,915,523 A | 12/1959 | Moore et al. |
| 2,981,731 A | 4/1961 | Moore et al. |
| 2,985,661 A | 5/1961 | Hien et al. |
| 3,267,107 A | 8/1966 | Sallay |
| 3,272,707 A | 9/1966 | Tedeschi |
| 3,449,330 A | 6/1969 | Guglielmetti et al. |
| 3,538,097 A | 11/1970 | Lowe et al. |
| 3,542,782 A | 11/1970 | Houlihan et al. |
| 3,849,561 A | 11/1974 | Junzo et al. |
| 3,884,911 A | 5/1975 | Shimada et al. |
| 3,912,740 A | 10/1975 | Zee-Chang et al. |
| 4,749,708 A | 6/1988 | Maroko |
| 4,761,417 A | 8/1988 | Maroko et al. |
| 4,761,477 A | 8/1988 | Ikekawa et al. |
| 4,925,943 A | 5/1990 | Kanmacher et al. |
| 4,938,949 A | 7/1990 | Borch et al. |
| 4,980,344 A | 12/1990 | Maroko |
| 5,106,863 A | 4/1992 | Hajos et al. |
| 5,126,351 A | 6/1992 | Luzzio et al. |
| 5,153,178 A | 10/1992 | Maroko |
| 5,190,753 A | 3/1993 | Behrens et al. |
| 5,244,903 A | 9/1993 | Wall et al. |
| 5,318,976 A | 6/1994 | Luzzi et al. |
| 5,639,759 A | 6/1997 | Magolda et al. |
| 5,646,283 A | 7/1997 | Suzuki et al. |
| 5,767,142 A | 6/1998 | LaVoie et al. |
| 5,770,617 A | 6/1998 | LaVoie et al. |
| 5,807,874 A | 9/1998 | LaVoie et al. |
| 5,981,541 A | 11/1999 | LaVoie et al. |
| 6,140,328 A | 10/2000 | LaVoie et al. |
| 6,509,344 B1 | 1/2003 | Cushman et al. |
| 6,740,650 B2 | 5/2004 | LaVoie et al. |
| 2004/0110760 A1 | 6/2004 | LaVoie et al. |
| 2005/0009824 A1 | 1/2005 | LaVoie et al. |
| 2005/0009826 A1 | 1/2005 | LaVoie et al. |
| 2005/0010046 A1 | 1/2005 | LaVoie et al. |

FOREIGN PATENT DOCUMENTS

| | | |
|---|---|---|
| EP | 0108147 B1 | 5/1984 |
| EP | 0496634 A1 | 7/1992 |
| GB | 2108955 A | 5/1983 |

(Continued)

OTHER PUBLICATIONS

Snyder et al.; J. Med. Liban 48(4): 208-214, 2000.*

(Continued)

*Primary Examiner*—Venkataraman Balasubramanian
(74) *Attorney, Agent, or Firm*—Viksnins Harris & Padys PLLP

(57) ABSTRACT

The invention provides compounds of the invention pharmaceutical compositions comprising a compound of the invention, processes for preparing compounds of the invention, intermediates useful for preparing compounds of the invention, and therapeutic methods for treating cancer and other topoisomerase mediated conditions.

86 Claims, No Drawings

FOREIGN PATENT DOCUMENTS

| | | |
|---|---|---|
| SU | 1530628 | 12/1989 |
| WO | WO-92/21661 A1 | 12/1992 |
| WO | WO-96/36612 A1 | 11/1996 |
| WO | WO-98/12181 A1 | 3/1998 |
| WO | WO-98/31673 A1 | 7/1998 |
| WO | WO-99/31067 A1 | 6/1999 |
| WO | WO-00/21537 A1 | 4/2000 |
| WO | WO-01/32631 A2 | 5/2001 |
| WO | WO-03/041660 A2 | 5/2003 |
| WO | WO-03/047505 A2 | 6/2003 |
| WO | WO-2004/014918 A1 | 2/2004 |

OTHER PUBLICATIONS

Turner et al., Current Pharmaceutical Design. 2, 209-224, 1996.*
Sugar et al., Diagn. Microbiol. Infect. Dis. 21: 129-133, 1995.*
Aguirre, J. M., et al., "Reaction of 1,2-diarylethylamides with ethyl polyphosphate(EPP): correlation of the von Braun, Ritter and Bischler-Napieralski reactions.", *Chemical Abstracts*, 111(13), Abstract No. 115004, (1989), 646.
Akiyama, Shin-Ichi, et al., "Isolation and Genetic Characterization of Human KB Cell Lines Resistant to Multiple Drugs", *Somatic Cell and Molecular Genetics*, 11(2), (1985), 117-126.
Andoh, Toshiwo, et al., "Characterization of a mammalian mutant with a camptothecin-resistant DNA topoisomerase I", *Proceedings of the National Academy of Sciences USA*, 84(16), (1987), 5565-5569.
Andoh, Toshiwo, et al., "Drug resistance mechanisms of topoisomerase I drugs", *Advances in Pharmacology, vol. 29B, DNA Topoisomerases: Topoisomerase- Targeting Drugs*, (1994), 93-103.
Arumugam, N., et al., "Synthesis of 7,8-Benzophenanthridines", *Indian Journal of Chemistry*, vol. 12, (1974), 664-667.
Badia, Dolores, et al., "Silicon-mediated isoquinoline synthesis: preparation and stereochemical characterization of 4-hydroxy-3-phenylisoquinolines", *Chemical Abstracts*, 117(13), Abstract No. 131034, (1992), 730.
Baezner, C., et al., "Uberfuhrung von o-nitro- und o,p-dinitro-benzylchlorid in acridinderivate", *Berichte der Deutschen Chemischen Gesellschaft*, 39, English Title—Conversion of o-nitro and o,p-dinitrobenzylchlroide into acridinic derivatives, (1906), 2438-2447.
Baezner, Carlo, "Uberfuhrung von o-nitro-und o, p-dinitro-benzyl chlorid in acridinderivate", *Berichte der Deutschen Chemischen Gesellschaft*, 37, English Title—Conversion of o-nitrobenzyl and chloride and o,p-dinitrobenzylchloride into acridine derivatives, (1904), 3077-3083.
Bhakuni, D. S., et al., "Protoberberine Alkaloids", *The Alkaloids*, vol. 28, Chapter 2, Academic Press, Inc., (1986), 95-181.
Bjornsti, Mary-Ann, et al., "Expression of human DNA topoisomerase I in yeast cells lacking yeast DNA topoisomerase I: restoration of sensitivity of the cells to the antitumor drug camptothecin", *Cancer Research*, 49, (1989), 6318-6323.
Bradsher, Charles K., et al., "Alpha-Acyl-o-tolunitriles as intermediates in the preparation of 3-substituted isoquinolines and 1-amino-2-benzopyrylium derivatives", *Chemical Abstracts*, 89(21), Abstract No. 89: 179810b,(1978), 590.
Brossi, Arnold, "Benzo[c]phenanthridine Alkaloids", *The Alkaloids, Chemistry and Pharmacology*, vol. XXV, Academic Press, Inc., (1985), 178-199.
Buu-Hoi, N. P., et al., "Carcinogenic Nitrogen Compounds, XV. Polysubstituted Angular Benacridines and Benzophenarsazines", *Chemical Abstracts*, 49(1), Abstract, col. 330, 10-Organic Chemistry, (1955), 329-330.
Buu-Hoi, N. G., et al., "The Chemistry of Carcinogenic Nitrogen Compounds. Part X. The Pfitzinger Reaction in the Synthesis of 1:2-Benzacridines", *Journal of the Chemical Society*, Letchworth GB, (1952), 279-281.
Buu-Hoi, N. G., "The chemistry of carcinogenic nitrogen compounds. Part V. Angular hydroxybenzacridines and hydroxydibenzacridines", *Journal of the Chemical Society*, Letchworth GB, (1950), 2096-2099.
Carmichael, James, "Evaluation of a tetrazolium-based semiautomated colorimetric assay: assessment of chemosensitivity testing", *Cancer Research*, 47, (1987), 936-42.

Chen, Allan Y., "A new mammalian DNA topoisomerase I poison Hoechst 33342: cytotoxicity and drug resistance in human cell cultures", *Cancer Research*, 53(6), (1993), 1332-1337.
Chen, Allan Y., et al., "DNA Minor Groove-Binding Ligands: A Different Class of Mammalian DNA Topoisomerase I Inhibitors", *Proceedings of the National Academy of Sciences of the United States of America*, 90, (1993),8131-8135.
Chen, Allan Y., et al., "DNA Topoisomerases: Essential Enzymes and Lethal Targets", *Annu. Rev. Pharmacol. Toxicol.*, 34, (1994), 191-218.
Cherif, Abdallah, et al., "N-(5,5-Diacetoxypent-1-yl)doxorubicin: a new intensely potent doxorubicin analogue", *Journal of Medicinal Chemistry*, 35, (Aug. 21, 1992), 3208-3214.
Croisy-Delcey, M., et al., "Synthesis and carcinogenic activity of oxidized benzacridines: potential metabolites of the strong carcinogen 7-methylbenz[c]acridine and of the inactive isomer 12-methylbenz[a]acridine.", *Journal of Medicinal Chemistry*, 26, (1983), 303-306.
Cushman, Mark, et al., "Synthesis and antitumor activity of structural analogues of the anticancer benzophenanthridine alkaloid fagaronine chloride", *Journal of Medicinal Chemistry*, 28, (1985), 1031-1036.
Cushman, Mark, et al., "Synthesis of New Indeno[1,2-c]isoquinolines: Cytotoxic Non-Camptothecin Topoisomerase I Inhibitors", *Journal of Medicinal Chemistry*, 43(20), (2000), 3688-3698.
D'Arpa, Peter, et al., "Topoisomerase-targeting antitumor drugs", *Biochimica et Biophysica Acta*, 989, (1989), 163-177.
Denizot, F., et al., "Rapid colorimetric assay for cell growth and survival. Modifications to the tetrazolium dye procedure giving improved sensitivity and reliability", *Journal of Immunological Methods*, 89, (1986), 271-277.
Denny, W. A., "Emerging DNA Topoisomerase Inhibitors as Anticancer Drugs", *Expert Opin. Emerg. Drugs*, 9(1), (2004), 105-133.
Dominguez, Esther, et al., "Dehydrogenation reactions of 1-substituted-3-aryltetrahydroisoquinoline derivatives", *Chemical Abstracts*, 101(11), Abstract No. 090742z, (1984), 624.
Dorofeenko, G. N., et al., "Synthesis of 3-aryl derivatives of 2-benzopyrylium salts with free alpha-positions", *Chemical Abstracts*, 74(15), Abstract No. 76295, (1971), 432.
Fitzgerald, J. J., et al., "Reaction of benzocyclobutene oxides with nitriles: synthesis of hypecumine and other 3-substituted isoquinolines", *Chemical Abstracts*, 122(7), Abstract No. 081704, (1995), 1128.
Fox, G. J., et al., "para-Bromination of Aromatic Amines: 4-Bromo-N,N-Dimethyl-3-(Trifluoromethyl)Aniline", *Organic Syntheses*, vol. 55, (1976), 20-23.
Fujii, Noboru, et al., "Induction of Mammalian DNA Topoisomerase I-mediated DNA Cleavage and DNA Winding by Bulgarein", *Journal of Biological Chemistry*, 268(18), (1993), 13160-13165.
Gallo, Robert C., et al., "Studies on the Antitumor Activity, Mechanism of Action, and Cell Cycle Effects of Camptothecin", *Journal of the National Cancer Institute*, vol. 46, No. 4, (1971), pp. 789-795.
Garcia, Alberto, et al., "A simple direct approach to 1-substituted 3-arylisoquinolines from deoxybenzoins and nitriles", *Chemical Abstracts*, 110(25), Abstract No. 231407u, (1989), 662.
Gatto, Barbara, "Identification of Topoisomerase I as the Cyctotoxic Target of the Protoberberine Alkaloid Coralyne", *Cancer Research*, 56(12), (1996), 2795-2800.
Giovanella, Beppino C., et al., "Complete growth inhibition of human cancer xenografts in nude mice by treatment with 20-(S)-camptothecin", *Cancer Research*, 51(11), (1991), 3052-3055.
Godowski, K. C., et al., "Free amine benzophenanthridine alkaloid compositions", *USPATFULL Database*, No. 95:20510, RN No. 218-38-2 (Benzo[c]phenanthradine), from U.S. Patent 5,395,615, (1995), 3 pages.
Goldman, Gustavo H., et al., "Differential poisoning of human and *Aspergillus nidulans* DNA topoisomerase I by bi- and terbenzimidazoles", *Biochemistry*, 36(21), (1997), 6488-6494.
Gopinath, K. W., et al., "Synthesis of Some 1:2- and 7:8-Benzophenanthridines", *Journal of the Chemical Society*, 78(2), (1958), 504-509.
Hahn, F. E., et al., "Berberine", *In: Antibiotics, Mechanism of Action of Antimicrobial and Antitumor Agents*, vol. III, J.W. Corcoran, et al., (eds.), Springer-Verlag, (1975), 577-584.

Halligan, Brian D., et al., "Purification and Characterization of a Type II DNA Topoisomerase from Bovine Calf Thymus", *The Journal of Biological Chemistry*, 260(4), (1985), 2475-2482.

Hoan, Nguyen, et al., "Syntheses from o-halogenated anisoles and phenetoles", *Chemical Abstracts*, 41(20), American Chemical Society, Abstract No. 6571bg, (1947), 2 Pages.

Hsiang, Yaw-Huei, et al., "Identification of Mammalian DNA Topoisomerase I as an Intracellular Target of the Anticancer Drug Camptothecin", *Cancer Research*, 48(7), (1988), 1722-1726.

IWAO, Masatomo, et al., "A Regiospecific Synthesis of Carbazoles via Consecutive Palladium-Catalyzed Cross-coupling and Aryne-Mediated Cyclization", *Heterocycles*, 36, (1993), 1483-1488.

Izmail'skii, V. A., et al., "Absorption Spectra of Molecular Complexes of Derivatives of Benzacridine and Dibenzacridine", *Chemical Abstracts*, 54(8), Abstract, col. 7335b, (1960), 3 pages.

Jacob, Juergen, et al., "Monooxygenase Induction by Various Xenobiotics and its Influence on Rat Liver Microsomal Metabolism of Chrysene in Comparison to Benz[a]anthracene", *Chemical Abstracts*, 107, Abstract No. 34760, (1987), 2 p.

Janin, Yves L., et al., "Synthesis and Evaluation of New 6-Amino-Susbtituted Benzo[c]phenanthridine Derivatives", *Journal of Medicinal Chemistry*, 36(23), (1993), 3686-3692.

Jayaraman, M., et al., "Synthesis of New Dihydroindeno [1,2-c] isoquinoline and Indenoisoquinolinium Chloride Topoisomerase I Inhibitors Having High in Vivo Anticancer Activity in the Hollow Fiber Animal Model", *Journal of Medicinal Chemistry*, 45(1), (2002), 242-249.

Kametani, Tetsuji, et al., "Studies on the synthesis of heterocyclic compounds, DCXXVII. The formation of 2,3,9,10-tetramethoxybenz[c]acridine by treatment of 6,7-dimethoxy-1-(4,5-dimethoxy-2-nitrophenethyl)-2-methylisoquinoline with triethyl phosphite", *Chemical and Pharmaceutical Bulletin*, 23(9), (1975), 2025-2028.

Kanmacher, I., et al., "Synthesis of Isoquino[1,2-b]quinazolines by Cycloaddition Reaction", *Chemical Abstracts*, 114, Abstract No. 207191, (1990), 4 pages.

Kar, G. K., et al., "Regioselective Thermal Cyclization of 3-substituted Arylenaminoimine hydrochlorides. A convenient method for the synthesis of Functionalized Polycyclic Quinoline Derivatives", *Chemical Abstracts*, 123, Abstract No. 111828, (1995), 1 p.

Kerrigan, J. E., et al., "5H-8,9-Dimethoxy-5-(2-N,N-dimethylaminoethyl)dibenzo[c, h][1,6]naphthyridin-6-ones and Related Compounds as TOP1-Targeting Agents: Influence of Structure on the Ternary Cleavable Complex Formation", *Bioorganic and Medicinal Chemistry Letters*, 13, (2003), 3395-3399.

Kessar, S V., et al., "Azasteroids. Part VII. Synthesis of 7-hydroxy-2-methoxy-7,8,9,10-tetrahydrobenzo[i]phenanthridine", *J. Chem. Soc.*, (1971), 259-261.

Kessar, S. V., et al., "New Routes to Condensed Polynuclear Compounds: Part X-Synthesis of Some Benzo[i]phenanthridines through Benzyne Cyclization", *Indian Journal of Chemistry*, 11, (1973), pp. 624-627.

Kim, J. S., et al., "Influence of steric factors on topoisomerase I inhibition and cytotoxicity of bisbenzimidazoles related to Hoechst 33342", *Proceedings of the 86th Annual Meeting of the American Association for Cancer Research*, 36, Abstract No. 2689, Toronto, Ontario, Canada,(Mar. 1995), p. 451.

Kim, J. S., et al., "Influence of steric factors on topoisomerase I inhibition and cytotoxicity of bisbenzimidazoles related to Hoechst 33342", *Abstract 7—Proceedings of the 3rd Annual Scientific Retreat of the Cancer Institute of New Jersey*, Princeton Marriott Forrestal Village, (1995), p. 28.

Kim, Jung S., et al., "Quantitative structure-activity relationships on 5-substituted terbenzimidazoles as topoisomerase I poisons and antitumor agents", *Bioorganic & Medicinal Chemistry*, 6(2), (1998), 4 pages.

Kim, J. S., et al., "Steric factors associated with the topoisomerase I inhibition and cytotoxicity of substituted bisbenzimidazoles", *Abstract 10- Proceedings of the American Association of Pharmaceutical Scientists Eastern Regional Meeting*, (1995), p. 27.

Kim, Jung S., et al., "Structure-activity Relationships of Benzimidazoles and Related Heterocycles as Topoisomerase I Poisons", *Bioorganic & Med. Chem.*, 4, (1996), pp. 621-630.

Kim, Jung S., "Substituted 2,5'-Bi-1H-benzimidazoles: Topoisomerase I Inhibition and Cytotoxicity", *Journal of Medicinal Chemistry*, 39(4), (1996), 992-998.

Kim, Jung S., et al., "Terbenzimidazoles: influence of 2"-, 4-, and 5-substituents on cytotoxicity and relative potency as topoisomerase I poisons", *Journal of Medicinal Chemistry*, 40(18), (1997), 2818-2824.

Kitamura, Tsugio, et al., "Isoquinoline derivatives from the Ritter-type reaction of vinyl cations", *Chemical Abstracts*, 102(1), Abstract No. 6157c, (1985).

Klopman, Gilles, et al., "Testing by Artificial Intelligence: Computational Alternatives to the Determination of Mutagenicity", *Chemical Abstracts*, 118, Abstract No. 17489, (1993), 1 p.

Knab, A. M., et al., "Mechanisms of Camptothecin Resistance in Yeast DNA Topoisomerase I Mutants", *Journal of Biological Chemistry*, 268(30), (1993), 22322-22330.

Lavoie, E. J., et al., "Structure-activity studies related to minor groove-binding ligands which inhibit mammalian DNA topoisomerase I", *Abstract 1—Proceedings of the 85th Annual Meeting of American Association for Cancer Research*, San Francisco, CA, (Apr. 1994), p. 2699.

Lee, Jeremy S., et al., "Coralyne binds tightly to both T A T and C G C$^+$—containing DNA triplexes", *Biochemistry*, 32(21), (1993), 5591-5597.

Liu, Leroy F., et al., "Cleavage of DNA by Mammalian DNA Topoisomerase II", *Journal of Biological Chemistry*, vol. 258, No. 24, (1983), 15365-15370.

Makhey, Darshan, "Coralyne and Related Compounds as Mammalian Topoisomerase I and Topoisomerase II Poisons", *Bioorganic & Medicinal Chemistry*, 4(6), (1996), 781-791.

Makhey, Darshan, "Protoberberine Alkaloids and Related Compounds as Dual Inhibitors of Mammalian Topoisomerase I and II", *Medicinal Chemistry Research*, 5(1), (1994), 1-12.

Meegalla, Sanath K., et al., "Synthesis and Pharmacological Evaluation of Isoindolo[1,2-b]quinazolinone and Isoindolo[2,1-a]benzimidazole Derivatives Related to the Antitumor Agent Batracylin", *J. Med. Chem.*, 37, (1994), pp. 3434-3439.

Memetzidis, G., et al., "Structure-affinity relationships of berbines or 5,6,13,13a-tetrahydro-8H-dibenzo[a,g]quinolizines at alpha-adrenoceptors", *European Journal of Medicinal Chemistry*, 26, (1991), 605-611.

Messmer, F. M., et al., "Fagaronine, a New Tumor Inhibitor Isolated from Fagara zanthoxyloides Lam. (Rutaceae)", *Journal of Pharmaceutical Sciences*, (Nov. 1972), 1858-1859.

Mohanty, N., et al., "New Therapeutic agents of the quinoline series. I. Fused quinolyl compounds", *Chemical Abstracts*, (1968), p. 1792.

Mosmann, Tim, "Rapid Colorimetric Assay for Cellular Growth and Survival: Application to Proliferation and Cytotoxicity Assays", *Journal of Immunological Methods*, 65(1-2), (1983), 55-63.

Nelson, Janis T., et al., "Proton and carbon-13 NMR spectra of fifteen substituted isoquinolines", *Chemical Abstracts*, 115(5), Abstract No. 048721, (1991), 753.

Peters, Dan, et al., "Synthesis of Various 5-Substituted Uracils", *Journal of Heterocyclic Chemistry*, 27, (1990), 2165-2173.

Pilch, Daniel S., et al., "A terbenzimidazole that preferentially binds and conformationally alters structurally distinct DNA duplex domains: a potential mechanism for topoisomerase I poisoning", *Proc. Nat'l. Acad. Sci. USA*, 94(25), (1997), 13565-13570.

Pilch, Daniel S., et al., "Biophysical Characterization of a Cytotoxic, Topoisomerase I Poison", *Abstract 8—Proceedings of the 3rd Annual Scientific Retreat of the Cancer Institute of New Jersey*, Princeton Marriott Forrestal Village, Princeton, NJ,(Jun. 1, 1995), 2 Pages.

Pilch, Daniel S., et al., "Characterizing the DNA binding modes of a topoisomerase I-poisoning terbenzimidazole: evidence for both intercalative and minor groove binding properties", *Drug Design and Discovery*, 13, (1996), 115-133.

Piper, J. R., et al., "Synthesis and Antifolate Activity of 5-Methyl-5,10-dideaza Analogues of Aminopterin and Folic Acid and an Alternative Synthesis of 5,10-Dideazatetrahydrofolic Acid, a Potent Inhibitor of Glycinamide Ribonucleotide Formyltransferase", *J. Med. Chem.*, 31, (1988), pp. 2164-2169.

Porai-Koshits, B. A., et al., "Imidazole derivatives Synthesis of some polybenzimidazoles", *J. Gen. Chem. USSR*, 23, As related in Chemical Abstracts, 48 (10) (1954), col. 12740, (1953), pp. 873-879.

Quast, Ulrich, et al., "Heterocyclic alpha-carbinolamines with the isoquinuclidine skeleton. 3. Benzoisoquinuclidines", *Chemical Abstracts*, 97 (21), Abstract No. 182180s, (1982), 806.

Ramesh, D., et al., "Studies on Polycyclic Azaarenes. 2. Sythesis of Trans-3,4-dihydroxy-3,-dihydrobenz[c]acridine and trans-8,9-dihydroxy-8,9-dihydrobenz[c]acridine", *Chemical Abstracts*, 108, Abstract No. 37626, (1988), 2 pages.

Ray, Jayanta K., et al., "A Facile and Convenient Method for the Synthesis of 8-methoxy-10,11-dihydronaphtho[1,2-b]quinolines", *Chemical Abstracts*, 92, Abstract No. 76254, (1980), 30-31.

Ruchelman, A. L., et al., "11H-isoquinol[4,3-c]cinnolin-12-ones: novel anticancer agents with potent topoisomerase I-targeting activity and cytotoxicity", *Bioorganic & Medicinal Chemistry*, 12, (2004), 795-806.

Ruchelman, Alexander L., et al., "Diaza- and Triazachrysenes: Potent Topoisomerase Targeting Agents with Exceptional Antitumor Activity against the Human Tumor Xenograft, MDA-MB-435", *Bioorganic & Medicinal Chemistry Letters*, vol. 12, (2002),333-3336.

Safaryan, G. P., et al., "2-Benzopyrylium salts. 25, Reaction of 2-benzopyrylium salts with some nucleophiles", *Chemical Abstracts*, 96(17), Abstract No. 142656z, (1982), 739.

Schiess, P., et al., "Thermolytic ring opening of acyloxybenzocyclobutenes: an efficient route to 3-substituted isoquinolines", *Chemical Abstracts*, 104(19), Abstract No. 168332z, (1986), 639.

Sethi, Manohar L., "Enzyme Inhibition VI: Inhibition of Reverse Transcriptase Activity by Protoberberine Alkaloids and Structure-Activity Relationships", *Journal of Pharmaceutical Sciences*, 72(5), (1983), 538-541.

Shcherbakova, I. V., et al., "2-Benzopyrilium salts. 35. Synthesis of the natural alkaloid dehydronorcoralydine and other substituted salts of dibenzo[a,g] quinolizine", *Chemical Abstracts*, 112 (19), Abstract No. 179554, (1990), 823.

Singh, S. K., et al., "Nitro and Amino Substitution in the D-Ring of 5-(2-Dimethylaminoethyl)-2,3-methylenedioxy-5H-dibenzo [c,h] [1,6] naphthyridin-6-ones: Effect on Topoisomerase-I Targeting Activity and Cytotoxicity", *Journal of Medicinal Chemistry*,46(11), (2003), 2254-2257.

Singh, Malvinder P., et al., "Synthesis and Sequence-Specific DNA Binding of a Topoisomerase Inhibitory Analog of Hoechst 33258 Designed for Altered Base and Sequence Recognition", *Chem. Res. Toxicol.*, 5, (1992), pp. 597-607.

Sotomayor, N., et al., "Oxidation reactions of 2'-functionalized 3-aryltetrahydro-and 3,4-dihydroisoquinolines", *Chemical Abstracts*, 124 (11), Abstract No. 145854, (1996), p. 1227.

Southard, G. L., et al., "Drug Delivery Devices", *USPATFULL Database*, No. 91:36238, RN No. 218-38-2 (Benzo[c]phenanthradine), from U.S. Patent 5,013,553, (1991), 2 pages.

Stermitz, Frank R., "Synthesis and Biological Activity of Some Antitumor Benzophenanthridinum Salts", *Journal of Medicinal Chemistry*, 18(7), (1975), 708-713.

Sun, Qun, et al., "Structure activity of novel topoisomerase I inhibitors related to Hoechst 33342", *Abstract 6—Proceedings of the American Association of Pharmaceutical Scientists Eastern Regional Meeting*, Hyatt Regency Hotel, New Brunswick, NJ, (Jun. 5-6, 1995), p. 25.

Sun, Qun, et al., "Structure Activity of Topoisomerase I Poisons Related to Hoechst 33342", *Bioorganic & Medicinal Chemistry Letters*, 4 (24), (1994), pp. 2871-2876.

Sun, Qun, et al., "Structure-activity studies related to minor groove-binding ligands which inhibit mammalian DNA topoisomerase I", *Cancer Institute of New Jersey's First Annual Scientific Retreat*, Abstract 2, Princeton Marriott Forrestal Village, Princeton, NJ, (Jun. 7, 1994), p. 66.

Sun, Qun, et al., "Synthesis and Evaluation of Terbenzimidazoles as Topoisomerase I Inhibitors", *Chemical Abstracts*, 123(15), Abstract No. 198740r, (1995), 1241.

Sun, Q., et al., "Synthesis and evaluation of terbenzimidazoles as topoisomerase I inhibitors", *Journal of Medicinal Chemistry*, 38(18), (1995), 3638-3644.

Sun, Qun, et al., "Synthesis and Pharmacological Evaluation of a Series of Novel DNA Topoisomerase I Inhibitors as Antitumor Agents", *Scientific Proceedings of 86th Annual Meeting of the American Association for Cancer Research*, Abstract 3, vol. 36, Toronto, Canada, (Mar. 1995).

Sun, Qun, et al., "Synthesis and pharmacological evaluation of a series of novel DNA topoisomerase I inhibitors as antitumor agents", *Abstract 5—Proceedings of the 3rd Annual Scientific Retreat of the Cancer Institute of New Jersey*, Princeton Marriott Forrestal Village, Princeton, NJ, (1995), p. 27.

Sun, Qun, et al., "Synthesis of Benzimidazo[2,1-a]isoquinolines and 5,6-Dihydrobenzimidazo[2,1-a]isoquinolines", *Syn. Lett., submitted*, Paper No. 7, (1995), 6 pages.

Tamura, H., et al., "Molecular cloning of a cDNA of a camptothecin-resistant human DNA topoisomerase I and identification of mutation sites", *Nucleic Acids Research*, 19 (1), (1991), pp. 69-75.

Tewey, K M., et al., "Adriamycin-induced DNA damage mediated by mammalian DNA topoisomerase II", *Science*, 226(4673), (1984), 466-8.

Vinogradov, A. E., et al., "Some properties of new DNA specific bisbenzimidazole fluorochromes without a piperazine ring", *Biotechnic & Histochemistry*, 68 (5), (1993), pp. 265-270.

Walterova, D., et al., "Isolation, Chemistry and Biology of Alkaloids from plants of Papaveraceae. Part XCV. Practical application of isotachophoresis in analysis of isoquinoline alkaloids", *Chemical Abstract*, vol. 104, No. 12, (1986), 454.

Wang, Li-Kai, et al., "Inhibition of Topoisomerase I Function by Coralyne and 5,6 -Dihydrocoralyne", *Chem. Res. Toxicol.*, 9, (1996), pp. 75-83.

Wang, Li-Kai, et al., "Inhibition of Topoisomerase I Function by Nitidine and Fagaronine", *Chem. Res. Toxicol.*, 6, (1993), pp. 813-818.

Wang, Huimin, et al., "Stimulation of topoisomerase II-mediated DNA damage via a mechanism involving protein thiolation", *Biochemistry*, 40(11), American Chemical Society, (2001), 3316-3323.

Waters, W. A., et al., "Reactions of Free Benzyl Radicals with Benz[a]- and Benz[c]acridine", *Chemical Abstracts*, 54 (4), Abstract, col. 3424b, (1960).

Wilson, W. D., et al., "Coralyne. Intercalation with DNA as a Possible Mechanism of Antileukemic Action", *Journal of Medicinal Chemistry*, 19(10), Communications to the Editor, (1976), 1261-1263.

Yadagiri, Bathini, et al., "Convenient Routes to Substituted Benzimidazoles and Imidazolo[4,5-b]Pyridines Using Nitrobenzene as Oxidant", *Synthetic Communications*, 20 (7), (1990), pp. 955-963.

Yamamoto, Yutaka, et al., "Reaction of 6H-1, 3-oxazin-6-one with benzyne giving isoquinoline derivatives", *Chemical Abstracts*, 118(7), Abstract No. 059563u,(1993),831.

Yamashita, Yoshinori, et al., "Induction of Mammalian DNA Topoisomerase I and II Mediated DNA Cleavage by Saintopin, a New Antitumor Agent from Fungus", *Biochemistry*, 30(24), (1991),5838-5845.

Yamashita, Yoshinori, "Induction of Mammalian DNA Topoisomerase I Mediated DNA Cleavage by Antitumor Indolocarbazole Derivatives", *Biochemistry*, 31(48), (1992), 12069-12075.

Zee-Cheng, K., et al., "Experimental Antileukemic Agents. Coralyne, Analogs, and Related Compounds", *Journal of Medicinal Chemistry*, 17(3), (1974), 347-351.

Zee-Cheng, K. Y., et al., "Practical Preparation of Coralyne Chloride", *Journal of Pharmaceutical Sciences*, 61 (6), (Jun. 1972), 969-971.

Zee-Cheng, R. K., et al., "Tetramethoxydibenzoquinolizinium Salts. Preparation and Antileukemic Activity of Some Positional and Structural Isomers of Coralyne", *Journal of Medicinal Chemistry*, 19(7), (1976), 882-886.

\* cited by examiner

CYTOTOXIC AGENTS

RELATED APPLICATIONS

This application is a continuation under 35 U.S.C. 111(a) of PCT/US02/36604, filed Nov. 14, 2002 and published in English on May 22, 2003 as WO 03/041653 A2, which claimed priority under 35 U.S.C. 119(e) of U.S. Provisional Application No. 60/332,733, filed Nov. 14, 2001, U.S. Provisional Application No. 60/333,040, filed Nov. 14, 2001, U.S. Provisional Application No. 60/332,698, filed Nov. 14, 2001, U.S. Provisional Application No. 60/333,051, filed Nov. 14, 2001, and U.S. Provisional Application No. 60/332,970, filed Nov. 14, 2001, which applications and publications are incorporated herein by reference.

BACKGROUND OF THE INVENTION

DNA-topoisomerases are enzymes which are present in the nuclei of cells where they catalyze the breaking and rejoining of DNA strands, which control the topological state of DNA. Recent studies also suggest that topoisomerases are also involved in regulating template supercoiling during RNA transcription. There are two major classes of mammalian topoisomerases. DNA-topoisomerase-I catalyzes changes in the topological state of duplex DNA by performing transient single-strand breakage-union cycles. In contrast, mammalian topoisomerase II alters the topology of DNA by causing a transient enzyme bridged double-strand break, followed by strand passing and resealing. Mammalian topoisomerase II has been further classified as Type II α and Type II β. The antitumor activity associated with agents which are topoisomerase poisons is associated with their ability to stabilize the enzyme-DNA cleavable complex. This drug-induced stabilization of the enzyme-DNA cleavable complex effectively converts the enzyme into a cellular poison.

Several antitumor agents in clinical use have potent activity as mammalian topoisomerase II poisons. These include adriamycin, actinomycin D, daunomycin, VP-16, and VM-26 (teniposide or epipodophyllotoxin). In contrast to the number of clinical and experimental drugs which act as topoisomerase II poisons, there are currently only a limited number of agents which have been identified as topoisomerase I poisons. Camptothecin and its structurally-related analogs are among the most extensively studied topoisomerase I poisons. Recently, bi- and terbenzimidazoles (Chen et al., *Cancer Res.* 1993, 53, 1332-1335; Sun et al., *J. Med. Chem.* 1995, 38, 3638-3644; Kim et al., *J. Med. Chem.* 1996, 39, 992-998), certain benzo[c]phenanthridine and protoberberine alkaloids and their synthetic analogs (Makhey et al., *Med. Chem. Res.* 1995, 5, 1-12; Janin et al., *J. Med. Chem.* 1975, 18, 708-713; Makhey et al., *Bioorg. & Med. Chem.* 1996, 4, 781-791), as well as the fungal metabolites, bulgarein (Fujii et al., *J. Biol. Chem.* 1993, 268, 13160-13165) and saintopin (Yamashita et al., *Biochemistry* 1991, 30, 5838-5845) and indolocarbazoles (Yamashita et al., *Biochemistry* 1992, 31, 12069-12075) have been identified as topoisomerase I poisons. Other topoisomerase poisons have been identified including certain benzo[i]phenanthridine and cinnoline compounds (see LaVoie et al., U.S. Pat. No. 6,140,328 (735.037WO1), and WO 01/32631 (735.044WO1)). Despite these reports there is currently a need for additional agents that are useful for treating cancer.

SUMMARY OF THE INVENTION

Applicant has discovered compounds that show inhibitory activity against topoisomerase I and/or topoisomerase II, and compounds that are effective cytotoxic agents against cancer cells, including drug-resistant cancer cells. Accordingly, the invention provides a compound of the invention which is a compound of formula I:

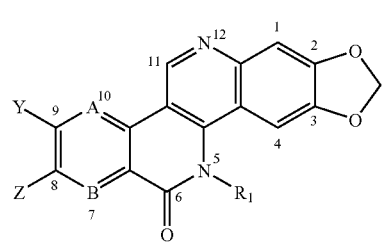

wherein:

A and B are independently N or CH;

Y and Z are independently hydroxy, $(C_1-C_6)$alkoxy, substituted $(C_1-C_6)$alkoxy, $(C_1-C_6)$alkanoyloxy, substituted $(C_1-C_6)$ alkanoyloxy, —O—P(=O)(OH)$_2$, or —O—C(=O)NR$_c$R$_d$; or Y and Z together with the ring carbon atoms to which they are attached form an alkylenedioxy ring with from 5 to 7 ring atoms;

R$_1$ is $(C_1-C_6)$alkyl; and

R$_c$ and R$_d$ are each independently $(C_1-C_6)$ alkyl or substituted $(C_1-C_6)$ alkyl; or R$_c$ and R$_d$ together with the nitrogen to which they are attached form a N'—$(C_1-C_6)$ alkylpiperazino, pyrrolidino, or piperidino ring, which ring can optionally be substituted with one or more aryl, heteroaryl, or heterocycle;

or a pharmaceutically acceptable salt thereof.

The invention also provides a compound of the invention which is a compound of formula II:

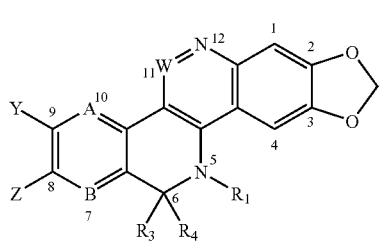

wherein:

A and B are independently N or CH;

W is N or CH;

R$_3$ and R$_4$ are both H, or R$_3$ and R$_4$ together are =O, =S, =NH or =N—R$_2$ wherein R$_2$ is $(C_1-C_6)$alkyl or substituted $(C_1-C_6)$alkyl;

Y and Z are independently hydroxy, $(C_1-C_6)$alkoxy, substituted $(C_1-C_6)$alkoxy, $(C_1-C_6)$alkanoyloxy, substituted $(C_1-C_6)$ alkanoyloxy, —O—P(=O)(OH)$_2$, or —O—C(=O)NR$_c$R$_d$; or Y and Z together with the ring carbon atoms to which they are attached form an alkylenedioxy ring with from 5 to 7 ring atoms;

$R_1$ is hydrogen or $(C_1-C_6)$alkyl; and $R_c$ and $R_d$ are each independently $(C_1-C_6)$ alkyl or substituted $(C_1-C_6)$ alkyl; or $R_c$ and $R_d$ together with the nitrogen to which they are attached form a N'—$(C_1-C_6)$ alkylpiperazino, pyrrolidino, or piperidino ring, which ring can optionally be substituted with one or more aryl, heteroaryl, or heterocycle;

provided that at least one or both A and B is N; and provided that when $R_3$ and $R_4$ are both H then W is CH;

or a pharmaceutically acceptable salt thereof.

The invention also provides a compound of the invention which is a compound of formula III:

III wherein:

X is O, S, NH, or =N—$R_2$ wherein $R_2$ is $(C_1-C_6)$alkyl or substituted $(C_1-C_6)$alkyl;

Y and Z are independently hydroxy, $(C_1-C_6)$alkoxy, substituted $(C_1-C_6)$alkoxy, $(C_1-C_6)$alkanoyloxy, substituted $(C_1-C_6)$ alkanoyloxy, —O—P(=O)(OH)$_2$, or —O—C(=O)NR$_c$R$_d$; or Y and Z together with the ring carbon atoms to which they are attached form an alkylenedioxy ring with from 5 to 7 ring atoms;

$R_1$ is hydrogen or $(C_1-C_6)$alkyl; and $R_c$ and $R_d$ are each independently $(C_1-C_6)$ alkyl or substituted $(C_1-C_6)$ alkyl; or $R_c$ and $R_d$ together with the nitrogen to which they are attached form a N'—$(C_1-C_6)$ alkylpiperazino, pyrrolidino, or piperidino ring, which ring can optionally be substituted with one or more aryl, heteroaryl, or heterocycle;

or a pharmaceutically acceptable salt thereof.

The invention also provides a compound of the invention which is a compound of formula IV:

IV wherein:

A and B are independently N or CH;

W is N or CH;

Y and Z are independently hydroxy, $(C_1-C_6)$alkoxy, substituted $(C_1-C_6)$alkoxy, $(C_1-C_6)$alkanoyloxy, substituted $(C_1-C_6)$ alkanoyloxy, —O—P(=O)(OH)$_2$, or —O—C(=O)NR$_c$R$_d$; or Y and Z together with the ring carbon atoms to which they are attached form an alkylenedioxy ring with from 5 to 7 ring atoms;

$R_1$ and $R_2$ are independently H, $(C_1-C_6)$alkyl or substituted $(C_1-C_6)$alkyl; or $R_1$ and $R_2$ together are =O or =S; and $R_c$ and $R_d$ are each independently $(C_1-C_6)$ alkyl or substituted $(C_1-C_6)$ alkyl; or $R_c$ and $R_d$ together with the nitrogen to which they are attached form a N'—$(C_1-C_6)$ alkylpiperazino, pyrrolidino, or piperidino ring, which ring can optionally be substituted with one or more aryl, heteroaryl, or heterocycle;

or a pharmaceutically acceptable salt thereof.

The invention also provides a compound of the invention which is a compound of formula V:

V wherein:

A and B are independently N or CH;

W is N or CH;

Y and Z are independently hydroxy, $(C_1-C_6)$alkoxy, substituted $(C_1-C_6)$alkoxy, $(C_1-C_6)$alkanoyloxy, substituted $(C_1-C_6)$ alkanoyloxy, —O—P(=O)(OH)$_2$, or —O—C(=O)NR$_c$R$_d$; or Y and Z together with the ring carbon atoms to which they are attached form an alkylenedioxy ring with from 5 to 7 ring atoms;

$R_1$ and $R_2$ are independently H, $(C_1-C_6)$alkyl, or substituted $(C_1-C_6)$alkyl; or $R_1$ and $R_2$ together are =O or =S; and $R_c$ and $R_d$ are each independently $(C_1-C_6)$ alkyl or substituted $(C_1-C_6)$ alkyl; or $R_c$ and $R_d$ together with the nitrogen to which they are attached form a N'—$(C_1-C_6)$ alkylpiperazino, pyrrolidino, or piperidino ring, which ring can optionally be substituted with one or more aryl, heteroaryl, or heterocycle;

or a pharmaceutically acceptable salt thereof.

The invention also provides a pharmaceutical composition comprising a effective amount of a compound of the invention in combination with a pharmaceutically acceptable diluent or carrier.

The invention also provides a method for modulating topoisomerase activity in a mammal in need of such treatment comprising administering to the mammal, an amount of a compound of the invention effective to provide a topoisomerase modulating effect.

The invention also provides a method of inhibiting cancer cell growth, comprising administering to a mammal afflicted with cancer, an amount of a compound of the invention, effective to inhibit the growth of said cancer cells.

The invention also provides a method comprising inhibiting cancer cell growth by contacting said cancer cell in vitro or in vivo with an amount of a compound of the invention, effective to inhibit the growth of said cancer cell.

The invention also provides a compound of the invention for use in medical therapy, preferably for use in treating cancer, for example, solid tumors, as well as the use of a compound of the invention for the manufacture of a medicament useful for the treatment of cancer, for example, solid tumors.

The invention also provides processes and novel intermediates disclosed herein which are useful for preparing compounds of the invention. Some of the compounds of the invention are useful to prepare other compounds of the invention.

DETAILED DESCRIPTION

The following definitions are used, unless otherwise described.

"$(C_1-C_6)$alkyl" denotes both straight and branched carbon chains with one or more, for example, 1, 2, 3, 4, 5, or 6, carbon atoms, but reference to an individual radical such as "propyl" embraces only the straight chain radical, a branched chain isomer such as "isopropyl" being specifically referred to.

"Substituted $(C_1-C_6)$alkyl" is an alkyl group of the formula $(C_1-C_6)$alkyl as defined above wherein one or more (e.g. 1 or 2) carbon atoms in the alkyl chain have been replaced with a heteroatom independently selected from —O—, —S— and NR— (where R is hydrogen or $C_1-C_6$alkyl) and/or wherein the alkyl group is substituted with from 1 to 5 substituents independently selected from cycloalkyl, substituted cycloalkyl, $(C_1-C_6)$alkoxycarbonyl (e.g. —CO$_2$Me), cyano, halo, hydroxy, oxo (=O), carboxy (COOH), aryloxy, heteroaryloxy, heterocyclooxy, nitro, and —NR$^a$R$^b$, wherein R$^a$ and R$^b$ may be the same or different and are chosen from hydrogen, alkyl, arylalkyl, heteroarylalkyl, heterocycloalkyl, cycloalkyl, substituted cycloalkyl, aryl, heteroaryl and heterocyclic. Substituted $(C_1-C_6)$alkyl groups are exemplified by, for example, groups such as hydroxymethyl, hydroxyethyl, hydroxypropyl, 2-aminoethyl, 3-aminopropyl, 2-methylaminoethyl, 3-dimethylaminopropyl, 2-carboxyethyl, hydroxylated alkyl amines, such as 2-hydroxyaminoethyl, and like groups. Preferred substituted $(C_1-C_6)$alkyl groups are $(C_1-C_6)$alkyl groups substituted with one or more substituents of the formula-NR$_a$R$_b$ where R$_a$ and R$_b$ together with the nitrogen to which they are attached form of nitrogen containing heterocyclic ring. Specific examples of such heterocyclic rings include piperazino, pyrrolidino, piperidino, morpholino, or thiomorpholino. Other preferred substituted $(C_1-C_6)$alkyl groups are $(C_1-C_6)$ alkyl groups substituted with one or more carbon-linked oxygen containing heterocyclic rings. Specific examples of such oxygenated heterocyclic rings are, for example, tetrahydrofuranyl, tetrahydropyranyl, 1,4-dioxanyl, and like groups.

"$(C_1-C_6)$alkoxy" refers to groups of the formula $(C_1-C_6)$ alkyl-O—, where $(C_1-C_6)$alkyl is as defined herein. Preferred alkoxy groups include, by way of example, methoxy, ethoxy, propoxy, iso-propoxy, n-butoxy, tert-butoxy, sec-butoxy, n-pentoxy, n-hexoxy, 1,2-dimethylbutoxy, and like groups.

"Substituted $(C_1-C_6)$alkoxy" refers to a substituted $(C_1-C_6)$alkyl-O— group wherein substituted $(C_1-C_6)$alkyl is as defined above. Substituted $(C_1-C_6)$alkoxy is exemplified by groups such as O—CH$_2$CH$_2$—NR$_a$R$_b$, O—CH$_2$CH$_2$—CHR$_a$R$_b$, or O—CH$_2$—CHOH—CH$_2$—OH, and like groups. Preferred substituted $(C_1-C_6)$alkoxy groups are $(C_1-C_6)$alkyl substituted with one or more substituents of the formula-NR$_a$R$_b$ where R$_a$ and R$_b$ together with the nitrogen to which they are attached form of a heterocyclic ring. Specific examples of such heterocyclic rings include piperazino, pyrrolidino, piperidino, morpholino, or thiomorpholino. Other preferred substituted $(C_1-C_6)$alkoxy groups are $(C_1-C_6)$alkoxy groups substituted with one or more carbon-linked oxygen containing heterocyclic rings. Specific examples of preferred oxygenated heterocyclic ring substituents are, for example, tetrahydrofuranyl, tetrahydropyranyl, 1,4-dioxanyl, and like groups. Specific examples of such oxygenated heterocyclic rings are, for example, tetrahydrofuranyl, tetrahydropyranyl, 1,4-dioxanyl, and like groups.

"$(C^1-C_6)$alkanoyloxy" includes, by way of example, formyloxy, acetoxy, propanoyloxy, iso-propanoyloxy, n-butanoyloxy, tert-butanoyloxy, sec-butanoyloxy, n-pentanoyloxy, n-hexanoyloxy, 1,2-dimethylbutanoyloxy, and like groups.

"Substituted $(C_1-C_6)$alkanoyloxy" refers to a $(C_1-C_6)$ alkanoyloxy group wherein one or more (e.g. 1 or 2) carbon atoms in the alkyl chain have been replaced with a heteroatom independently selected from —O—, —S— and NR— (where R is hydrogen or $C_1-C_6$alkyl) and/or wherein the alkyl group is substituted with from 1 to 5 substituents independently selected from cycloalkyl, substituted cycloalkyl, $(C_1-C_6)$alkoxycarbonyl (e.g. —CO$_2$Me), cyano, halo, hydroxy, oxo (=O), carboxy (COOH), aryloxy, heteroaryloxy, heterocyclooxy, nitro, and —NR$^a$R$^b$, wherein R$^a$ and R$^b$ may be the same or different and are chosen from hydrogen, alkyl, arylalkyl, heteroarylalkyl, heterocycloalkyl, cycloalkyl, substituted cycloalkyl, aryl, heteroaryl and heterocyclic Substituted $(C_1-C_6)$alkanoyloxy is exemplified by groups such as —O—C(=O)CH$_2$—NR$_a$R$_b$, and O—C(=O)—CHOH—CH$_2$—OH. Preferred substituted $(C_1-C_6)$alkanoyloxy groups are groups wherein the alkyl group is substituted with one or more nitrogen and oxygen containing heterocyclic rings such as piperazino, pyrrolidino, piperidino, morpholino, thiomorpholino, tetrahydrofuranyl, tetrahydropyranyl, 1,4-dioxanyl, and like groups.

Aryl denotes a phenyl radical or an ortho-fused bicyclic carbocyclic radical having about nine to ten ring atoms in which at least one ring is aromatic. Examples of aryl include phenyl, indenyl, and naphthyl.

Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) and quinolyl (or its N-oxide).

The term "heterocycle" refers to a monovalent saturated or partially unsaturated cyclic non-aromatic group which contains at least one heteroatom, preferably 1 to 4 heteroatoms, selected from nitrogen (NR$_x$, wherein R$_x$ is hydrogen, alkyl, or a direct bond at the point of attachment of the heterocycle group), sulfur, phosphorus, and oxygen within at least one cyclic ring and which may be monocyclic or multi-cyclic. Such heterocycle groups preferably contain from 3 to 10 atoms. The point of attachment of the heterocycle group may be a carbon or nitrogen atom. This term also includes heterocycle groups fused to an aryl or heteroaryl group, provided the point of attachment is on a non-aromatic heteroatom-containing ring. Representative heterocycle groups include, by way of example, pyrrolidinyl, piperidinyl, piperazinyl, imidazolidinyl, morpholinyl, indolin-3-yl, 2-imidazolinyl, 1,2,3,4-tetrahydroisoquinolin-2-yl, quinuclidinyl and the like.

"Aryloxy" refers to a group of the formula aryl-O—, where aryl is as defined herein. Examples of aryloxy groups include, phenoxy and 1-naphthyloxy.

"Heteroaryloxy" refers to a group of the formula heteroaryl-O—, where heteroaryl is as defined herein. Examples of heteroaryloxy groups include, 3-piperidyloxy, 3-furyloxy, and 4-imidazolidinyl.

"Heterocyclooxy" refers to a group of the formula heterocycle-O—, where heterocycle is as defined herein. Examples of heterocyclooxy groups include, 4-morpholinooxy and 3-tetrahydrofuranyloxy.

"Arylalkyl" refers to a group of the formula aryl-$(C_1-C_6)$alkyl-, where aryl and $(C_1-C_6)$alkyl are as defined herein.

"Heteroarylalkyl" refers to a group of the formula heteroaryl-$(C_1-C_6)$alkyl-, where heteroaryl and $(C_1-C_6)$alkyl are as defined herein.

"Heterocycloalkyl" refers to a group of the formula heterocycle-$(C_1-C_6)$alkyl-, where heterocycle and $(C_1-C_6)$alkyl are as defined herein.

Specific and preferred values listed below for radicals, substituents, and ranges, are for illustration only; they do not exclude other defined values or other values within defined ranges for the radicals and substituents.

The Following Specific Values, Preferred Values, and Discussion Relate to Compounds of Formula I.

Specifically, $(C_1-C_6)$alkyl can be methyl, ethyl, propyl, isopropyl, butyl, iso-butyl, sec-butyl, pentyl, 3-pentyl, or hexyl.

A specific value for A is CH.

Another specific value for A is N.

A specific value for B is N.

Another specific value for B is CH.

A specific value for Y is OH.

Another specific value for Y is $(C_1-C_6)$alkoxy.

Another specific value for Y is —OCH$_3$.

Another specific value for Y is substituted $(C_1-C_6)$alkoxy.

Another specific value for Y is —OCH$_2$CH$_2$OH.

Another specific value for Y is —OCH$_2$CH$_2$OCH$_2$CH$_3$.

Another specific value for Y is —O—CH$_2$—CHOH—CH$_2$—OH.

Another specific value for Y is —O—CH$_2$CH$_2$—NR$_a$R$_b$ wherein R$_a$ and R$_b$ are hydrogen or $(C_1-C_6)$alkyl.

Another specific value for Y is —O—CH$_2$CH$_2$—NR$_a$R$_b$ wherein R$_a$ and R$_b$ together with the nitrogen to which they are attached form a piperazino, pyrrolidino, piperidino, morpholino, or thiomorpholino ring.

Another specific value for Y is —O—C(=O)CH$_2$—NR$_a$R$_b$.

Another specific value for Y is —O—C(=O)—CHOH—CH$_2$—OH.

Another specific value for Y is $(C_1-C_6)$alkyl substituted with one or more tetrahydrofuranyl, tetrahydropyranyl, or 1,4-dioxanyl rings.

Another specific value for Y is —O—C(=O)CH$_2$—NR$_a$R$_b$.

A specific value for Z is OH.

Another specific value for Z is $(C_1-C_6)$alkoxy.

Another specific value for Z is OCH$_3$.

Another specific value for Z is substituted $(C_1-C_6)$alkoxy.

Another specific value for Z is —OCH$_2$CH$_2$OH.

Another specific value for Z is —OCH$_2$CH$_2$OCH$_2$CH$_3$.

Another specific value for Z is —O—CH$_2$—CHOH—CH$_2$—OH.

Another specific value for Z is —O—CH$_2$CH$_2$—NR$_a$R$_b$ wherein R$_a$ and R$_b$ are hydrogen or $(C_1-C_6)$alkyl.

Another specific value for Z is —O—CH$_2$CH$_2$—NR$_a$R$_b$ wherein R$_a$ and R$_b$ together with the nitrogen to which they are attached form a piperazino, pyrrolidino, piperidino, morpholino, or thiomorpholino ring.

Another specific value for Z is —O—C(=O)—CHOH—CH$_2$—OH.

Another specific value for Z is $(C_1-C_6)$alkyl substituted with one or more tetrahydrofuranyl, tetrahydropyranyl, or 1,4-dioxanyl rings.

Another specific value for Z is —O—C(=O)CH$_2$—NR$_a$R$_b$.

A specific value for $R_1$ is $(C_1-C_6)$alkyl.

Another specific value for $R_1$ is methyl, ethyl, propyl, isopropyl, n-butyl, iso-butyl, n-pentyl, isopentyl, or n-hexyl.

A preferred compound of formula (I) is the compound 12-ethyl-2,3-dimethoxy-12H-8,10-dioxa-6,12-diaza-cyclopenta[b]chrysen-13-one, 12-butyl-2,3-dimethoxy-12H-8,10-dioxa-6,12-diaza-cyclopenta[b]chrysen-13-one, or a pharmaceutically acceptable salt thereof.

Certain compounds of formula (I) can function as prodrugs for other compounds of formula (I). For example, a compound of formula (I) wherein Y and/or Z is —O—P(=O)(OH)$_2$, or —O—C(=O)NR$_c$R$_d$; can function as a prodrug for a corresponding compound of formula (I) wherein Y and or Z is hydroxy. Accordingly, a specific sub set of compounds of formula (I) are compounds wherein Y and/or Z is —O—P(=O)(OH)$_2$, or —O—C(=O)NR$_c$R$_d$. A particularly preferred compound is a compound of formula (I) wherein Y and/or Z is —O—P(=O)(OH)$_2$. Another preferred compound is a compound of formula (I) wherein Y and/or Z is —O—C(=O)NR$_c$R$_d$, wherein R$_c$ and/or R$_d$ is $(C_1-C_6)$alkyl substituted with one or more —NR$_e$R$_f$ wherein R$_e$ and R$_f$ are each independently $(C_1-C_6)$alkyl. Another preferred compound is a compound of formula (I) wherein Y and/or Z is —O—C(=O)NR$_c$R$_d$, wherein R$_c$ and R$_d$ together with the nitrogen to which they are attached form a N'-(alkyl)piperazino, pyrrolidino, or piperidino ring. A more preferred compound is a compound of formula (I) wherein Y and/or Z is —O—C(=O)NR$_c$R$_d$, wherein R$_c$ and R$_d$ together with the nitrogen to which they are attached form a piperidino ring, which ring is optionally substituted with an N-linked heterocycle (e.g. piperidino) ring.

The present invention provides compounds formula I and a method of making compounds of formula I wherein $R_1$ is $(C_1-C_6)$alkyl or substituted $(C_1-C_6)$alkyl comprising reacting the compound of formula I where $R_1$ is H with a suitable nitrogen alkylating agent, such as an $(C_1-C_6)$alkyl halide or substituted $(C_1-C_6)$alkyl halide, to form a corresponding $(C_1-C_6)$alkyl or substituted $(C_1-C_6)$alkyl compound. It is understood by one skilled in the art that the lactam nitrogen atom can be conveniently synthetically manipulated and efficiently converted into related useful compounds by, for example, preparing intermediate compounds with a protected N atom and which protected nitrogen atom can be deprotected and subsequently alkylated to provide the above mentioned alkylated nitrogen compounds.

A compound of formula I can be prepared by subjecting a corresponding intermediate of formula A to suitable cyclization conditions, for example, by treatment with palladium acetate and tri-o-tolylphosphine, as illustrated in Scheme 1 below. A compound of formula I can also be prepared by subjecting a corresponding intermediate of formula B to conditions suitable for the formation of the ring system, for example, by treatment with a suitable tin reagent, as illustrated in Scheme 2 below. Compounds of the present invention include intermediates of formulas A and B.

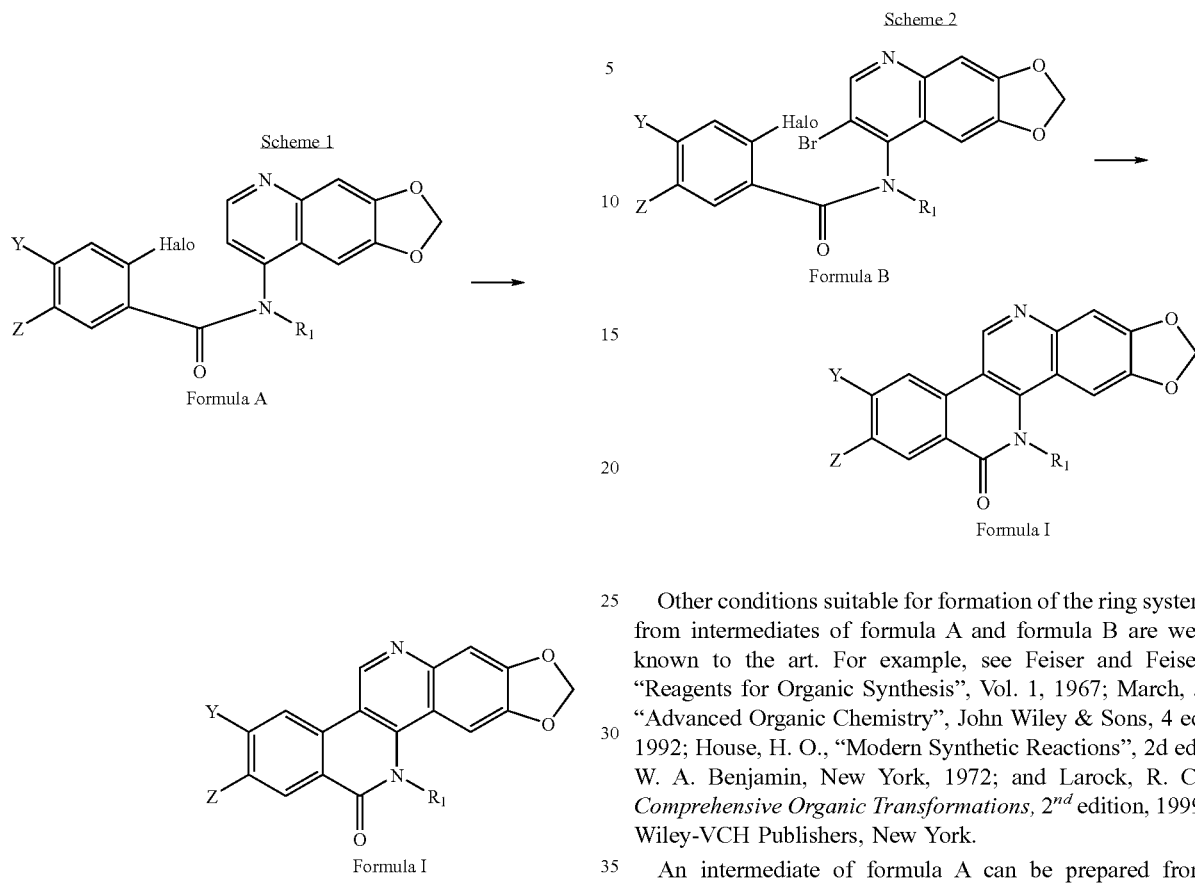

Other conditions suitable for formation of the ring system from intermediates of formula A and formula B are well known to the art. For example, see Feiser and Feiser, "Reagents for Organic Synthesis", Vol. 1, 1967; March, J. "Advanced Organic Chemistry", John Wiley & Sons, 4 ed. 1992; House, H. O., "Modern Synthetic Reactions", 2d ed., W. A. Benjamin, New York, 1972; and Larock, R. C., Comprehensive Organic Transformations, $2^{nd}$ edition, 1999, Wiley-VCH Publishers, New York.

An intermediate of formula A can be prepared from readily available starting materials using procedures that are known in the art, or can be prepared using the procedures illustrated below.

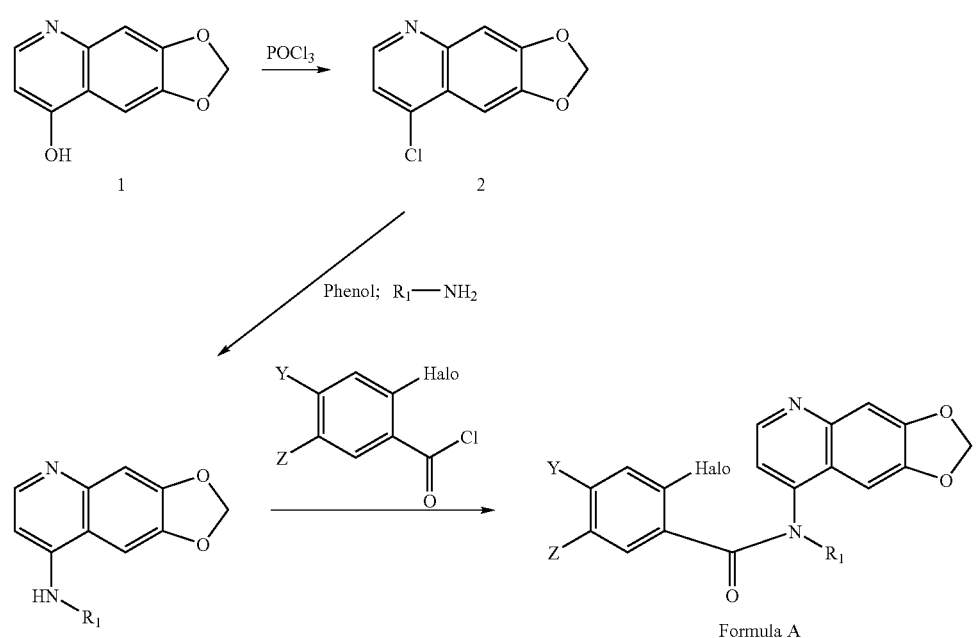

Chlorination of Compound 1 yields chloro-compound 2, which can be converted to the corresponding amine by treatment with phenol and subsequent reaction with the appropriate amine. The resulting amine can be acylated with the appropriately substituted acylchloride to provide the intermediate of formula A.

An intermediate of formula B can be prepared from readily available starting materials using procedures that are known in the art, or can be prepared using procedures illustrated below.

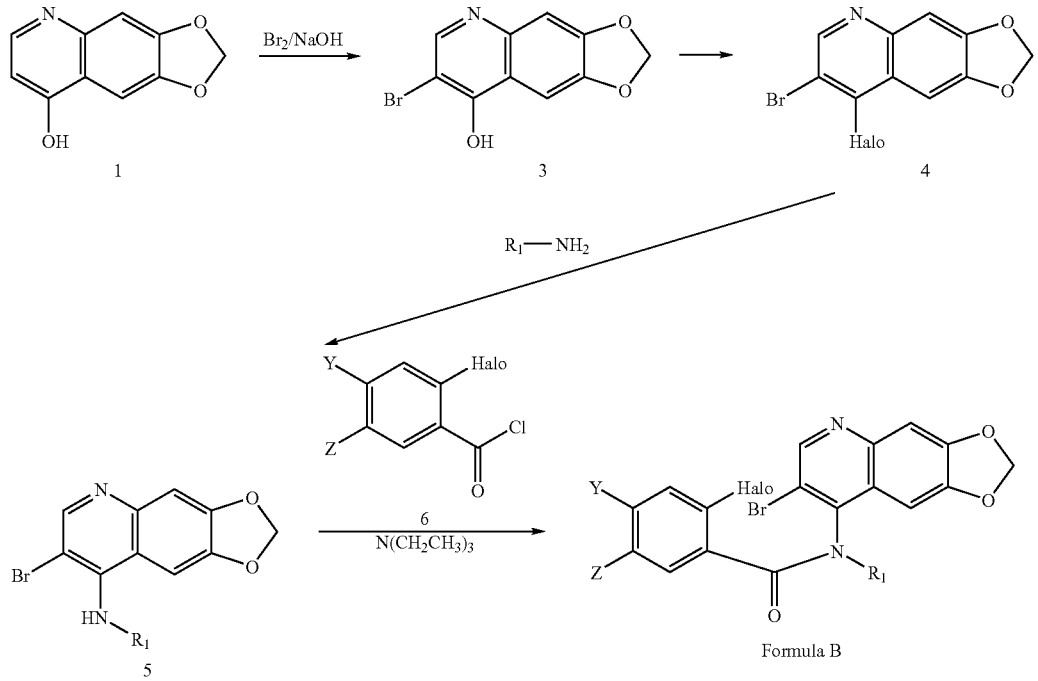

Bromination of compound 1 provides compound 3, which can be converted to halo-compound 4 using procedures known in the art. Reaction with a suitable amine or ammonium salt provides amino compound 5, which can be converted to an intermediate of formula B by treatment with a suitable acid chloride 6.

The Following Specific Values, Preferred Values, and Discussion Relate to Compounds of Formula II.

Specific and preferred values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl.

Specifically, $(C_1-C_6)$alkoxy can be methoxy, ethoxy, propoxy, isopropoxy, butoxy, iso-butoxy, sec-butoxy, pentoxy, 3-pentoxy, or hexoxy.

A specific value for A is CH.
Another specific value for A is N.
A specific value for B is N.
Another specific value for B is CH.
A specific value for W is N.
Another specific value for W is CH.
A specific value for Y is OH.
Another specific value for Y is $(C_1-C_6)$alkoxy.
Another specific value for Y is —OCH$_3$.
Another specific value for Y is substituted $(C_1-C_6)$alkoxy.
Another specific value for Y is —OCH$_2$CH$_2$OH.
Another specific value for Y is —OCH$_2$CH$_2$OCH$_2$CH$_3$.
Another specific value for Y is —O—CH$_2$—CHOH—CH$_2$—OH.
Another specific value for Y is —O—CH$_2$CH$_2$—NR$_a$R$_b$ wherein R$_a$ and R$_b$ are hydrogen or $(C_1-C_6)$alkyl.
Another specific value for Y is —O—CH$_2$CH$_2$—NR$_a$R$_b$ wherein R$_a$ and R$_b$ together with the nitrogen to which they are attached form a piperazino, pyrrolidino, piperidino, morpholino, or thiomorpholino ring.
Another specific value for Y is —O—C(=O)CH$_2$—NR$_a$R$_b$.
Another specific value for Y is —O—C(=O)—CHOH—CH$_2$—OH.
Another specific value for Y is $(C_1-C_6)$alkyl substituted with one or more tetrahydrofuranyl, tetrahydropyranyl, or 1,4-dioxanyl rings.
Another specific value for Y is —O—C(=O)CH$_2$—NR$_a$R$_b$.
A specific value for Z is OH.
Another specific value for Z is $(C_1-C_6)$alkoxy.
Another specific value for Z is OCH$_3$.
Another specific value for Z is substituted $(C_1-C_6)$alkoxy.
Another specific value for Z is —OCH$_2$CH$_2$OH.
Another specific value for Z is —OCH$_2$CH$_2$OCH$_2$CH$_3$.
Another specific value for Z is —O—CH$_2$—CHOH—CH$_2$—OH.
Another specific value for Z is —O—CH$_2$CH$_2$—NR$_a$R$_b$ wherein R$_a$ and R$_b$ are hydrogen or $(C_1-C_6)$alkyl.
Another specific value for Z is —O—CH$_2$CH$_2$—NR$_a$R$_b$ wherein R$_a$ and R$_b$ together with the nitrogen to which they are attached form a piperazino, pyrrolidino, piperidino, morpholino, or thiomorpholino ring.

Another specific value for Z is —O—C(=O)—CHOH—CH$_2$—OH.

Another specific value for Z is (C$_1$-C$_6$)alkyl substituted with one or more tetrahydrofuranyl, tetrahydropyranyl, or 1,4-dioxanyl rings.

Another specific value for Z is —O—C(=O)CH$_2$—NR$_a$R$_b$.

A specific value for both R$_3$ and R$_4$ is H.

A specific value for R$_3$ and R$_4$ together is =O.

Another specific value for R$_3$ and R$_4$ together is =S.

Another specific value for R$_3$ and R$_4$ together is =NH.

Another specific value for R$_3$ and R$_4$ together is =N—R$_2$.

Another specific value for R$_3$ and R$_4$ together is =N—R$_2$ where R$_2$ is (C$_1$-C$_6$)alkyl.

Another specific value for R$_3$ and R$_4$ together is =N—R$_2$ where R$_2$ is substituted (C$_1$-C$_6$)alkyl.

A specific value for R$_1$ is hydrogen.

Another specific value for R$_1$ is (C$_1$-C$_6$)alkyl.

Another specific value for R$_1$ is isobutyl.

Another specific value for R$_1$ is n-butyl.

Another specific value for R$_1$ is isopentyl.

A specific value for R$_2$ is a (C$_1$-C$_6$)alkyl substituted with one or more hydroxy, mercapto, carboxy, amino, piperazinyl, pyrrolidinyl, piperidinyl, morpholinyl, thiomorpholinyl, tetrahydrofuranyl, tetrahydropyranyl, or 1,4-dioxanyl groups.

Another specific value for R$_2$ is a (C$_1$-C$_6$)alkyl with from 2 to 4 carbon atoms and substituted with one to two groups selected from hydroxy, mercapto, carboxy, amino, piperazinyl, pyrrolidinyl, piperidinyl, morpholinyl, thiomorpholinyl, tetrahydrofuranyl, tetrahydropyranyl, or 1,4-dioxanyl.

Another specific value for R$_2$ is —CH$_2$CH$_2$—NR$_a$R$_b$ wherein R$_a$ and R$_b$ are hydrogen or (C$_1$-C$_6$)alkyl.

Another specific value for R$_2$ is —CH$_2$CH$_2$—NR$_a$R$_b$ wherein R$_a$ and R$_b$ together with the nitrogen to which they are attached form a piperazino, pyrrolidino, piperidino, morpholino, or thiomorpholino ring.

A preferred compound of formula (II) is the compound 12-butyl-2,3-dimethoxy-12H-8,10-dioxa-4,5,6,12-tetra-azacyclopenta[b]chrysen-13-one; 12-butyl-2,3-dimethoxy-12H-8,10-dioxa-1,5,6,12-tetraaza-cyclopenta[b]chrysen-13-one; 12-butyl-2,3-dimethoxy-12H-8,10-dioxa-1,4,5,6,12-penta-azacyclopenta[b]chrysen-13-one; or a pharmaceutically acceptable salt thereof.

Certain compounds of formula (II) can function as prodrugs for other compounds of formula (II). For example, a compound of formula (II) wherein Y and/or Z is —O—P(=O)(OH)$_2$, or —O—C(=O)NR$_c$R$_d$; can function as a prodrug for a corresponding compound of formula (II) wherein Y and or Z is hydroxy. Accordingly, a specific sub set of compounds of formula (II) are compounds wherein Y and/or Z is —O—P(=O)(OH)$_2$, or —O—C(=O)NR$_c$R$_d$. A particularly preferred compound is a compound of formula (II) wherein Y and/or Z is —O—P(=O)(OH)$_2$. Another preferred compound is a compound of formula (II) wherein Y and/or Z is —O—C(=O)NR$_c$R$_d$, wherein R$_c$ and/or R$_d$ is (C$_1$-C$_6$)alkyl substituted with one or more —NR$_e$R$_f$ wherein R$_e$ and R$_f$ are each independently (C$_1$-C$_6$)alkyl. Another preferred compound is a compound of formula (II) wherein Y and/or Z is —O—C(=O)NR$_c$R$_d$, wherein R$_c$ and R$_d$ together with the nitrogen to which they are attached form a N'-(alkyl)piperazino, pyrrolidino, or piperidino ring. A more preferred compound is a compound of formula (II) wherein Y and/or Z is —O—C(=O)NR$_c$R$_d$, wherein R$_c$ and R$_d$ together with the nitrogen to which they are attached form a piperidino ring, which ring is optionally substituted with an N-linked heterocycle (e.g. piperidino) ring.

The present invention provides compounds formula II and a method of making compounds of formula II wherein R$_1$ is such as (C$_1$-C$_6$)alkyl or substituted (C$_1$-C$_6$)alkyl comprising reacting the compound of formula II where R$_1$ is H with a suitable nitrogen alkylating agent, such as an (C$_1$-C$_6$)alkyl halide or substituted (C$_1$-C$_6$)alkyl halide, to form a corresponding (C$_1$-C$_6$)alkyl or substituted (C$_1$-C$_6$)alkyl compound. It is understood by one skilled in the art that the lactam nitrogen atom can be conveniently synthetically manipulated and efficiently converted into related useful compounds by, for example, preparing intermediate compounds with a protected N atom and which protected nitrogen atom can be deprotected and subsequently alkylated to provide the above mentioned alkylated nitrogen compounds.

A compound of formula II can be prepared by subjecting a corresponding intermediate of formula A to suitable cyclization conditions; for example, by treatment with palladium acetate and tri-o-tolylphosphine, as illustrated in Scheme 1 below. A compound of formula II can be prepared by subjecting a corresponding intermediate of formula B to conditions suitable for the formation of the tetracyclic ring system; for example by treatment with a suitable tin reagent, as illustrated in Scheme 2 below.

Scheme 1

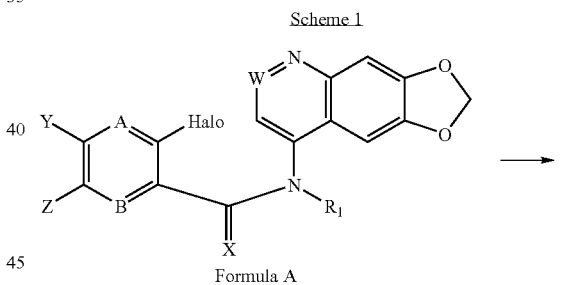

Formula A

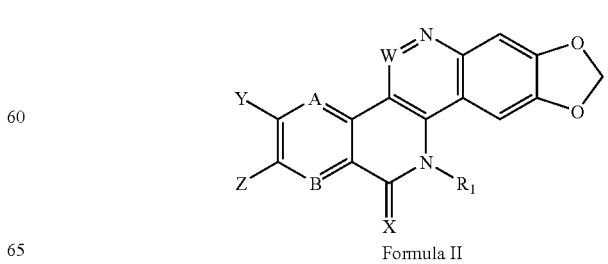

Formula II

Scheme 2

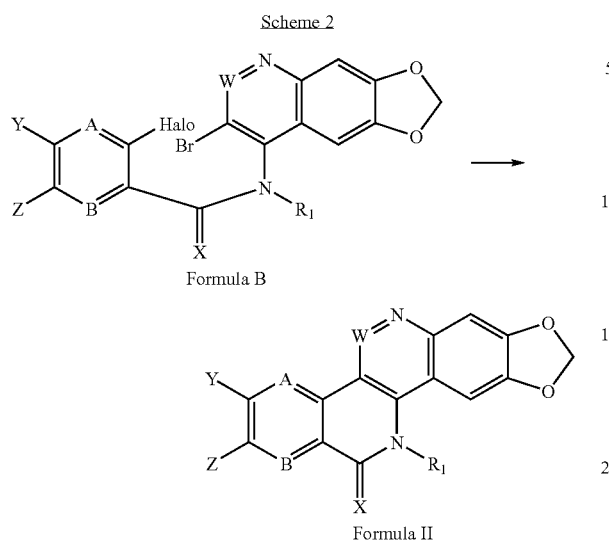

Other conditions suitable for formation of the ring system from intermediates of formula A and formula B are well known to the art. For example, see Feiser and Feiser, "Reagents for Organic Synthesis", Vol. 1, 1967; March, J. "Advanced Organic Chemistry", John Wiley & Sons, $4^{th}$ ed., 1992; House, H. O., "Modern Synthetic Reactions", 2d ed., W. A. Benjamin, New York, 1972; and Larock, R. C., *Comprehensive Organic Transformations*, $2^{nd}$ ed., 1999, Wiley-VCH Publishers, New York.

An intermediate of formula A can be prepared from readily available starting materials using procedures that are known in the art, or can be prepared using procedures illustrated below.

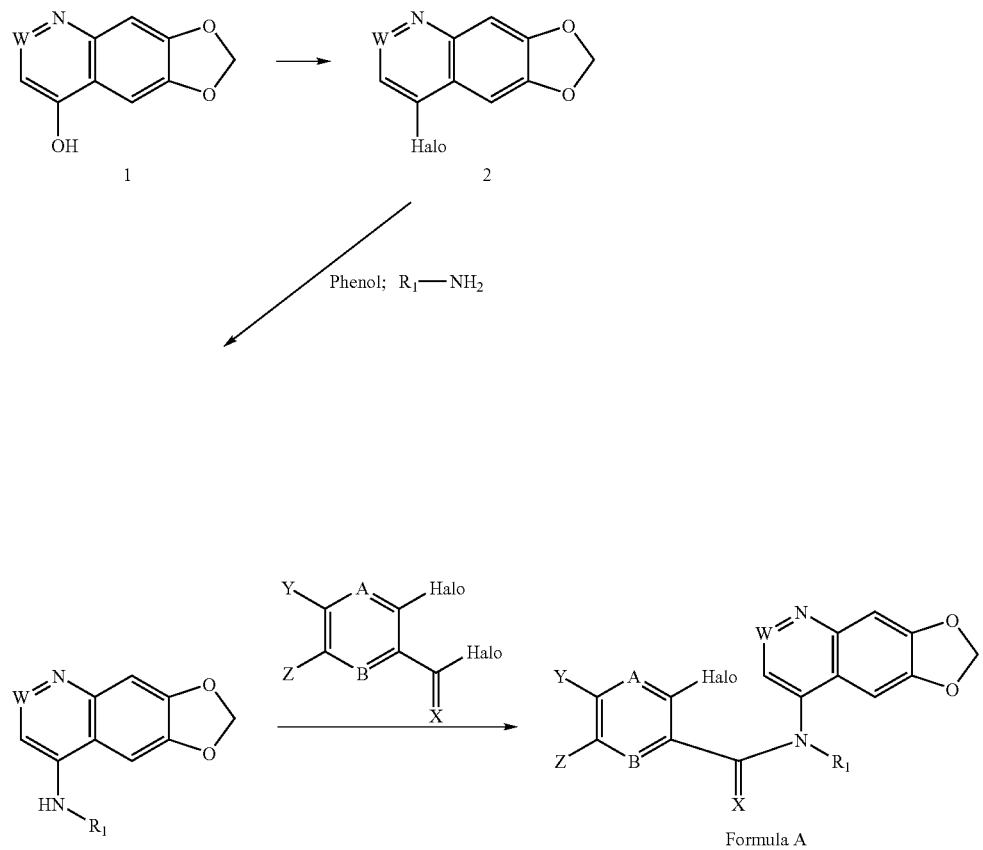

Similarly, an intermediate of formula B can be prepared from readily available starting materials using procedures that are known in the art, or can be prepared using procedures illustrated below.

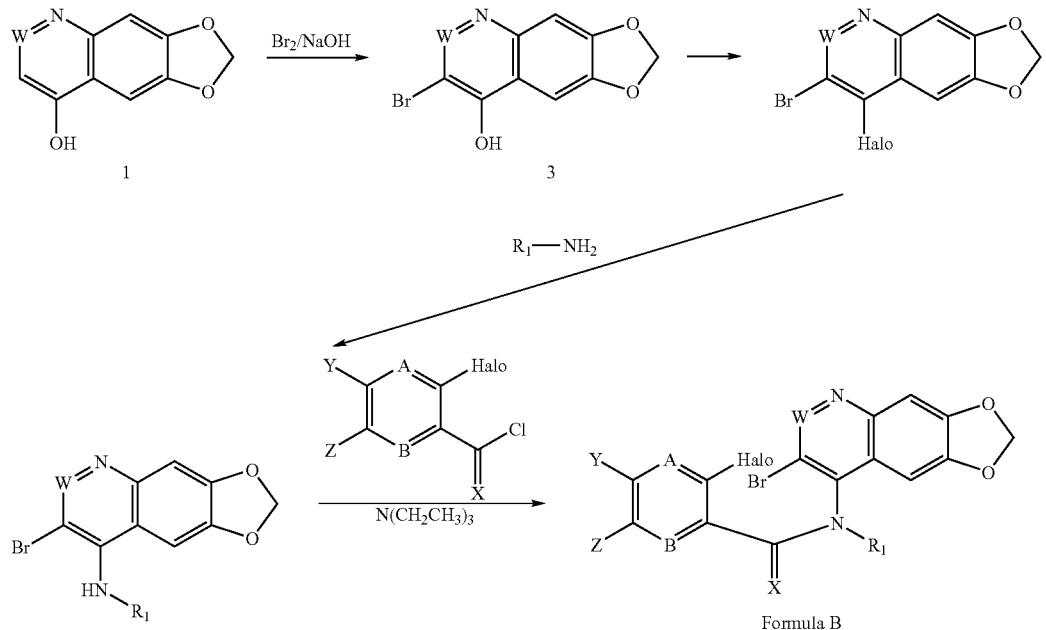

An alternative route to the formation of 5,6-dihydro derivatives of formula II involves either reduction of the lactam or desulfurization of the thioamide as illustrated by the following. Additionally, one can modify compounds of formula II to provide other compounds of formula II as illustrated below.

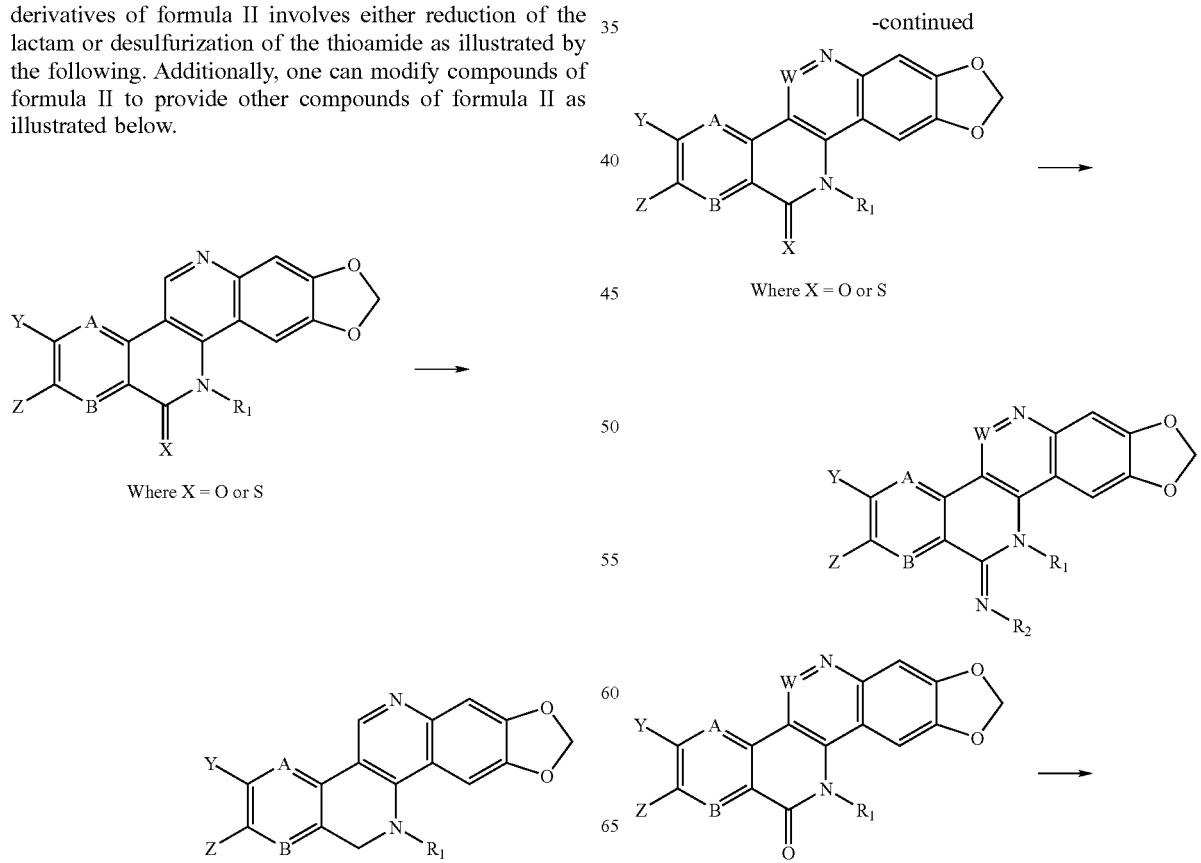

-continued

[Chemical structure diagram showing a polycyclic compound with labels W, N, Y, A, Z, B, X, N, R₁, O, O, and note "Where X = S, NR₂"]

The Following Specific Values, Preferred Values, and Discussion Relate to Compounds of Formula III.

Specifically, $(C_1-C_6)$alkyl can be methyl, ethyl, propyl, isopropyl, butyl, iso-butyl, sec-butyl, pentyl, 3-pentyl, or hexyl.

Specifically, $(C_1-C_6)$alkoxy can be methoxy, ethoxy, propoxy, isopropoxy, butoxy, iso-butoxy, sec-butoxy, pentoxy, 3-pentoxy, or hexoxy.

A specific value for X is =O.
Another specific value for X is =S.
Another specific value for X is =NH.
Another specific value for X is =N—R$_2$.
Another specific value for X is =N—R$_2$ where R$_2$ is $(C_1-C_6)$alkyl.
Another specific value for X is =N—R$_2$ where R$_2$ is substituted $(C_1-C_6)$alkyl.
A specific value for Y is OH.
Another specific value for Y is $(C_1-C_6)$alkoxy.
Another specific value for Y is —OCH$_3$.
Another specific value for Y is substituted $(C_1-C_6)$alkoxy.
Another specific value for Y is —OCH$_2$CH$_2$OH.
Another specific value for Y is —OCH$_2$CH$_2$OCH$_2$CH$_3$.
Another specific value for Y is —O—CH$_2$—CHOH—CH$_2$—OH.
Another specific value for Y is —O—CH$_2$CH$_2$—NR$_a$R$_b$ wherein R$_a$ and R$_b$ are hydrogen or $(C_1-C_6)$alkyl.
Another specific value for Y is —O—CH$_2$CH$_2$—NR$_a$R$_b$ wherein R$_a$ and R$_b$ together with the nitrogen to which they are attached form a piperazino, pyrrolidino, piperidino, morpholino, or thiomorpholino ring.
Another specific value for Y is —O—C(=O)CH$_2$—NR$_a$R$_b$.
Another specific value for Y is —O—C(=O)—CHOH—CH$_2$—OH.
Another specific value for Y is $(C_1-C_6)$alkyl substituted with one or more tetrahydrofuranyl, tetrahydropyranyl, or 1,4-dioxanyl rings.
Another specific value for Y is —O—C(=O)CH$_2$—NR$_a$R$_b$.
A specific value for Z is OH.
Another specific value for Z is $(C_1-C_6)$alkoxy.
Another specific value for Z is OCH$_3$.
Another specific value for Z is substituted $(C_1-C_6)$alkoxy.
Another specific value for Z is —OCH$_2$CH$_2$OH.
Another specific value for Z is —OCH$_2$CH$_2$OCH$_2$CH$_3$.
Another specific value for Z is —O—CH$_2$—CHOH—CH$_2$—OH.
Another specific value for Z is —O—CH$_2$CH$_2$—NR$_a$R$_b$ wherein R$_a$ and R$_b$ are hydrogen or $(C_1-C_6)$alkyl.
Another specific value for Z is —O—CH$_2$CH$_2$—NR$_a$R$_b$ wherein R$_a$ and R$_b$ together with the nitrogen to which they are attached form a piperazino, pyrrolidino, piperidino, morpholino, or thiomorpholino ring.
Another specific value for Z is —O—C(=O)—CHOH—CH$_2$—OH.
Another specific value for Z is $(C_1-C_6)$alkyl substituted with one or more tetrahydrofuranyl, tetrahydropyranyl, or 1,4-dioxanyl rings.
Another specific value for Z is —O—C(=O)CH$_2$—NR$_a$R$_b$.
A specific value for R$_1$ is methyl, ethyl, propyl, or isopropyl.

A preferred compound of formula (III) is the compound 12-butyl-2,3-dimethoxy-12H-8,10-dioxa-5,6,12-triaza-cyclopenta[b]chrysen-13-one, 12-isobutyl-2,3-dimethoxy-12H-8,10-dioxa-5,6,12-triaza-cyclopenta[b]chrysen-13-one, or a pharmaceutically acceptable salt thereof.

Certain compounds of formula (III) can function as prodrugs for other compounds of formula (III). For example, a compound of formula (III) wherein Y and/or Z is —O—P(=O)(OH)$_2$, or —O—C(=O)NR$_c$R$_d$; can function as a prodrug for a corresponding compound of formula (III) wherein Y and or Z is hydroxy. Accordingly, a specific sub set of compounds of formula (III) are compounds wherein Y and/or Z is —O—P(=O)(OH)$_2$, or —O—C(=O)NR$_c$R$_d$. A particularly preferred compound is a compound of formula (III) wherein Y and/or Z is —O—P(=O)(OH)$_2$. Another preferred compound is a compound of formula (III) wherein Y and/or Z is —O—C(=O)NR$_c$R$_d$, wherein R$_c$ and/or R$_d$ is $(C_1-C_6)$alkyl substituted with one or more —NR$_e$R$_f$ wherein R$_e$ and R$_f$ are each independently $(C_1-C_6)$alkyl. Another preferred compound is a compound of formula (III) wherein Y and/or Z is —O—C(=O)NR$_c$R$_d$, wherein R$_c$ and R$_d$ together with the nitrogen to which they are attached form a N'-(alkyl)piperazino, pyrrolidino, or piperidino ring. A more preferred compound is a compound of formula (III) wherein Y and/or Z is —O—C(=O)NR$_c$R$_d$, wherein R$_c$ and R$_d$ together with the nitrogen to which they are attached form a piperidino ring, which ring is optionally substituted with an N-linked heterocycle (e.g. piperidino) ring.

The present invention provides compounds formula III and a method of making compounds of formula III wherein R$_1$ is such as $(C_1-C_6)$alkyl or substituted $(C_1-C_6)$alkyl comprising reacting the compound of formula I where R$_1$ is H with a suitable nitrogen alkylating agent, such as an $(C_1-C_6)$alkyl halide or substituted $(C_1-C_6)$alkyl halide, to form a corresponding $(C_1-C_6)$alkyl or substituted $(C_1-C_6)$alkyl compound. It is understood by one skilled in the art that the lactam nitrogen atom can be conveniently synthetically manipulated and efficiently converted into related useful compounds by, for example, preparing intermediate compounds with a protected N atom and which protected nitrogen atom can be deprotected and subsequently alkylated to provide the above mentioned alkylated nitrogen compounds.

A compound of formula III can be prepared by subjecting a corresponding intermediate of formula A to suitable cyclization conditions; for example, by treatment with palladium acetate and tri-o-tolylphosphine, as illustrated in Scheme 1 below. A compound of formula III can also be prepared by subjecting a corresponding intermediate of formula B to conditions suitable for the formation of the ring system; for example by treatment with a suitable tin reagent, as illustrated in Scheme 2 below. Compounds of the present invention include intermediates of formulas A and B.

Scheme 1

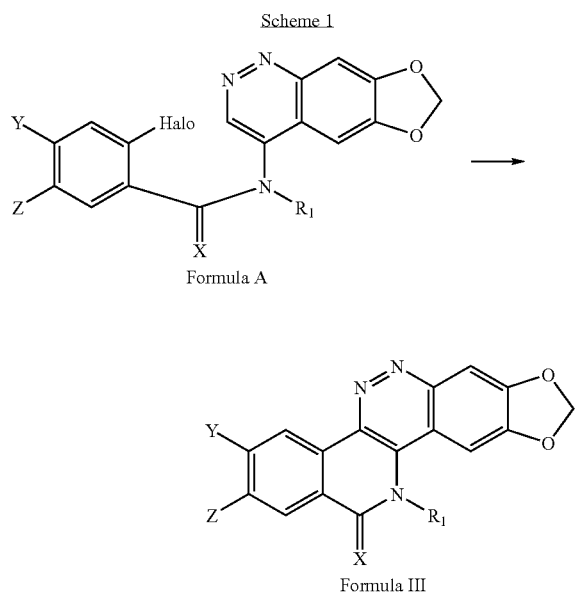

Formula A

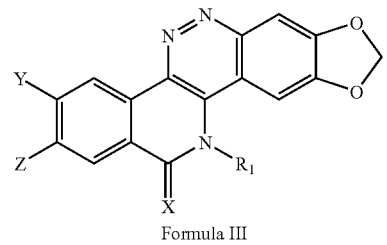

Formula III

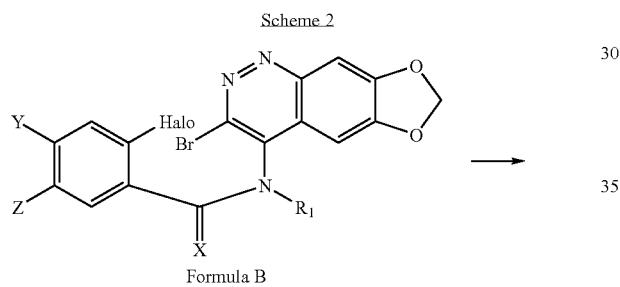

Formula III

Scheme 2

Other conditions suitable for formation of the ring system from intermediates of formula A and formula B are well known to the art. For example, see Feiser and Feiser, "Reagents for Organic Synthesis", Vol. 1, 1967; March, J. "Advanced Organic Chemistry", John Wiley & Sons, 4<sup>th</sup> ed., 1992; House, H. O., "Modern Synthetic Reactions", 2d ed., W. A. Benjamin, New York, 1972; and Larock, R. C., *Comprehensive Organic Transformations*, 2$^{nd}$ ed., 1999, Wiley-VCH Publishers, New York.

An intermediate of formula A can be prepared from readily available starting materials using procedures that are known in the art, or can be prepared using procedures illustrated below.

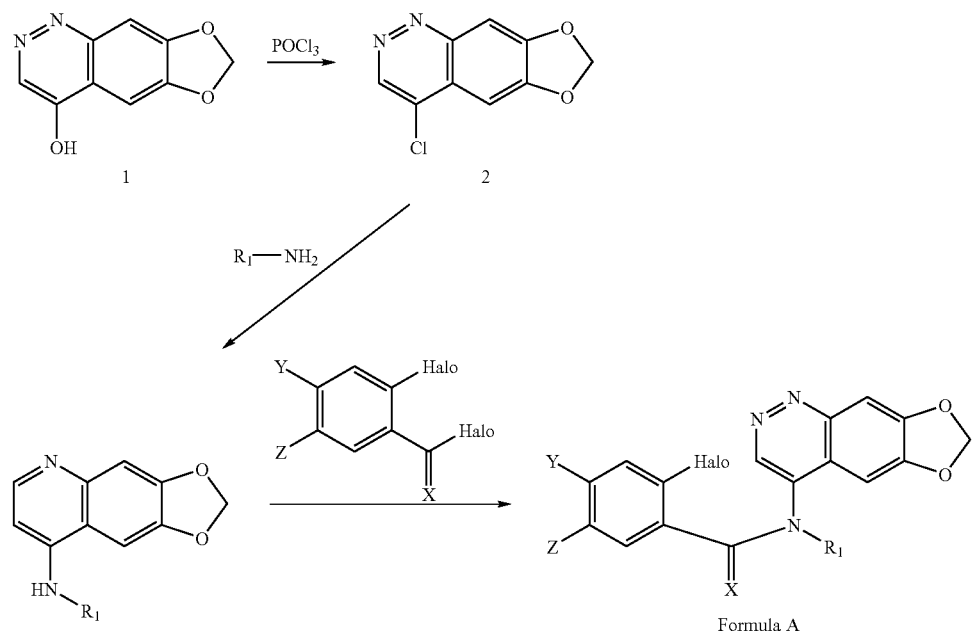

Similarly, an intermediate of formula B can be prepared from readily available starting materials using procedures that are known in the art, or can be prepared using procedures illustrated below.

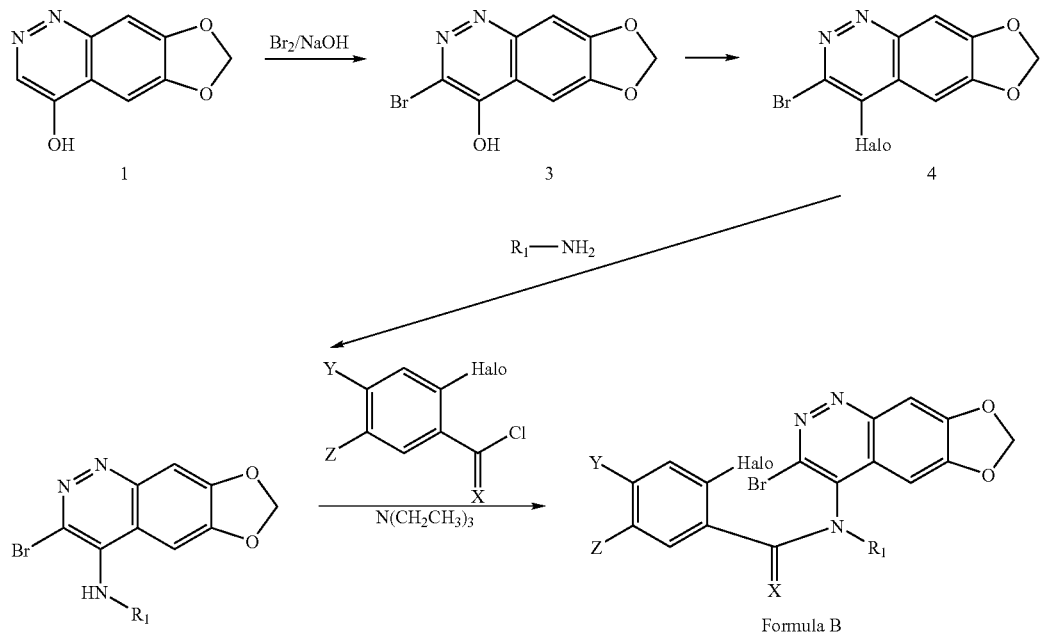

Alternatively, one can modify compounds of formula III to form related derivatives of formula III as illustrated by the following.

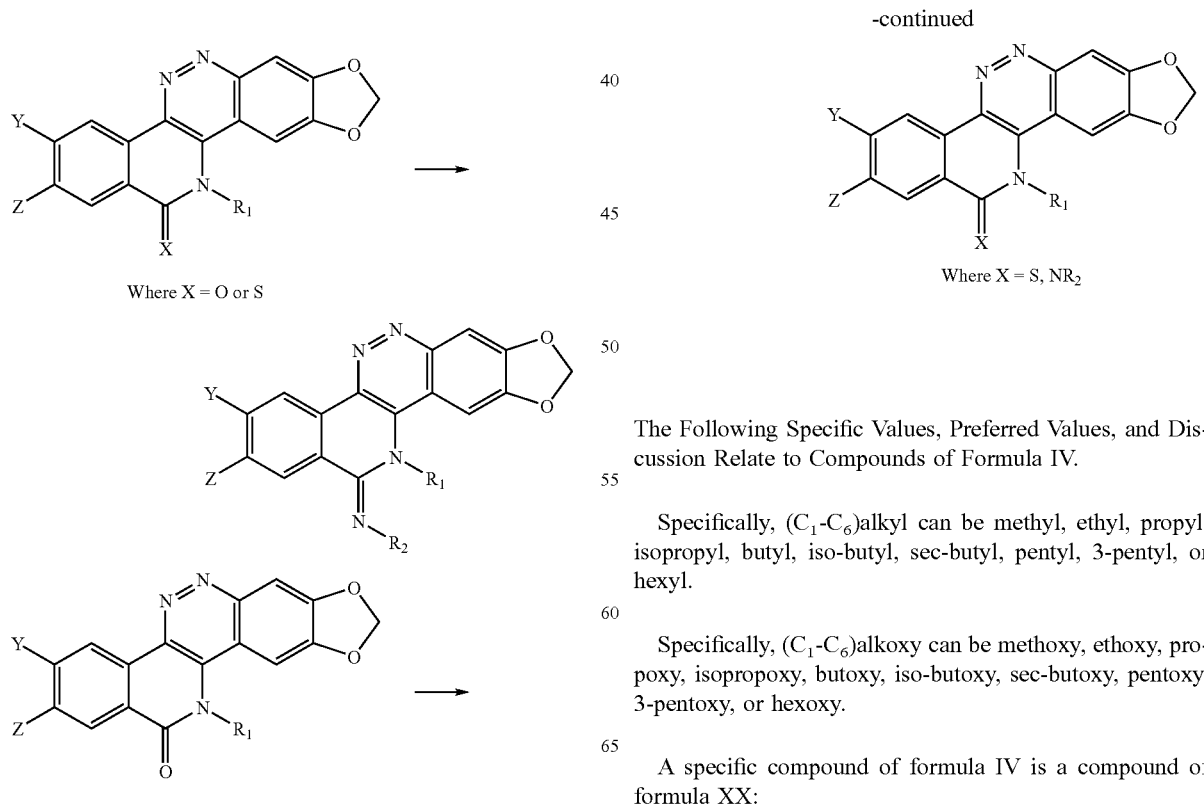

The Following Specific Values, Preferred Values, and Discussion Relate to Compounds of Formula IV.

Specifically, $(C_1$-$C_6)$alkyl can be methyl, ethyl, propyl, isopropyl, butyl, iso-butyl, sec-butyl, pentyl, 3-pentyl, or hexyl.

Specifically, $(C_1$-$C_6)$alkoxy can be methoxy, ethoxy, propoxy, isopropoxy, butoxy, iso-butoxy, sec-butoxy, pentoxy, 3-pentoxy, or hexoxy.

A specific compound of formula IV is a compound of formula XX:

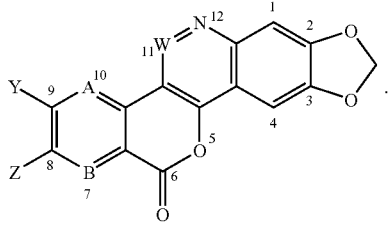

Another specific compound of formula IV is a compound of formula XXI:

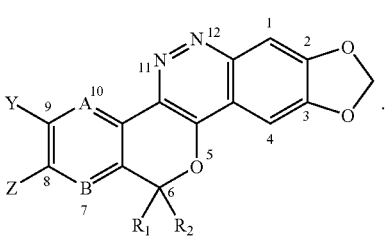

A specific value for W is N.
Another specific value for W is CH.
A specific value for A is CH.
Another specific value for A is N.
A specific value for B is N.
Another specific value for B is CH.
A specific value for Y is OH.
Another specific value for Y is $(C_1-C_6)$alkoxy.
Another specific value for Y is —$OCH_3$.
Another specific value for Y is substituted $(C_1-C_6)$alkoxy.
Another specific value for Y is —$OCH_2CH_2OH$.
Another specific value for Y is —$OCH_2CH_2OCH_2CH_3$.
Another specific value for Y is —O—$CH_2$—CHOH—$CH_2$—OH.
Another specific value for Y is —O—$CH_2CH_2$—$NR_aR_b$ wherein $R_a$ and $R_b$ are hydrogen or $(C_1-C_6)$alkyl.
Another specific value for Y is —O—$CH_2CH_2$—$NR_aR_b$ wherein $R_a$ and $R_b$ together with the nitrogen to which they are attached form a piperazino, pyrrolidino, piperidino, morpholino, or thiomorpholino ring.
Another specific value for Y is —O—C(=O)$CH_2$—$NR_aR_b$.
Another specific value for Y is —O—C(=O)—CHOH—$CH_2$—OH.
Another specific value for Y is $(C_1-C_6)$alkyl substituted with one or more tetrahydrofuranyl, tetrahydropyranyl, or 1,4-dioxanyl rings.
Another specific value for Y is —O—C(=O)$CH_2$—$NR_aR_b$.
A specific value for Z is OH.
Another specific value for Z is $(C_1-C_6)$alkoxy.
Another specific value for Z is $OCH_3$.
Another specific value for Z is substituted $(C_1-C_6)$alkoxy.
Another specific value for Z is —$OCH_2CH_2OH$.
Another specific value for Z is —$OCH_2CH_2OCH_2CH_3$.
Another specific value for Z is —O—$CH_2$—CHOH—$CH_2$—OH.
Another specific value for Z is —O—$CH_2CH_2$—$NR_aR_b$ wherein $R_a$ and $R_b$ are hydrogen or $(C_1-C_6)$alkyl.
Another specific value for Z is —O—$CH_2CH_2$—$NR_aR_b$ wherein $R_a$ and $R_b$ together with the nitrogen to which they are attached form a piperazino, pyrrolidino, piperidino, morpholino, or thiomorpholino ring.
Another specific value for Z is —O—C(=O)—CHOH—$CH_2$—OH.
Another specific value for Z is $(C_1-C_6)$alkyl substituted with one or more tetrahydrofuranyl, tetrahydropyranyl, or 1,4-dioxanyl rings.
Another specific value for Z is —O—C(=O)$CH_2$—$NR_aR_b$.
A specific value for $R_1$ or $R_2$ is a $(C_1-C_6)$alkyl substituted with one or more hydroxy groups.
Another specific value for $R_1$ or $R_2$ is a $(C_1-C_6)$alkyl substituted with one hydroxy group.
Another specific value for $R_1$ or $R_2$ is a $(C_1-C_6)$alkyl substituted with one or more mercapto groups.
Another specific value for $R_1$ or $R_2$ is a $(C_1-C_6)$alkyl substituted with one mercapto group.
Another specific value for $R_1$ or $R_2$ is a $(C_1-C_6)$alkyl substituted with one or more carboxy groups.
Another specific value for $R_1$ or $R_2$ is a $(C_1-C_6)$alkyl substituted with one carboxy group.
Another specific value for $R_1$ or $R_2$ is a $(C_1-C_6)$alkyl substituted with one or more $NR_aR_b$ groups.
Another specific value for $R_1$ or $R_2$ is a $(C_1-C_6)$alkyl substituted with one $NR_aR_b$ group.
Another specific value for $R_1$ or $R_2$ is a $(C_1-C_6)$alkyl substituted with one or more $NH_2$ groups.
Another specific value for $R_1$ or $R_2$ is a $(C_1-C_6)$alkyl substituted with one $NH_2$ group.
Another specific value for $R_1$ or $R_2$ is a $(C_1-C_6)$alkyl substituted with one or more hydroxy, mercapto, carboxy, amino, piperazinyl, pyrrolidinyl, piperidinyl, morpholinyl, thiomorpholinyl, tetrahydrofuranyl, tetrahydropyranyl, or 1,4-dioxanyl groups.
Another specific value for $R_1$ or $R_2$ is a $(C_1-C_6)$alkyl with from 2 to 4 carbon atoms and substituted with one to two groups selected from hydroxy, mercapto, carboxy, amino, piperazinyl, pyrrolidinyl, piperidinyl, morpholinyl, thiomorpholinyl, tetrahydrofuranyl, tetrahydropyranyl, or 1,4-dioxanyl.
Another specific value for $R_1$ or $R_2$ is 2-hydroxymethyl.
Another specific value for $R_1$ or $R_2$ is 2-hydroxyethyl.
Another specific value for $R_1$ or $R_2$ is 3-hydroxypropyl.
Another specific value for $R_1$ or $R_2$ is 2-hydroxypropyl.
Another specific value for $R_1$ or $R_2$ is H.
Another specific value for $R_1$ or $R_2$ is —$CH_2$—CHOH—$CH_2$—OH.
Another specific value for $R_1$ or $R_2$ is —$CH_2CH_2$—$NR_aR_b$ wherein $R_a$ and $R_b$ are hydrogen or $(C_1-C_6)$alkyl.
Another specific value for $R_1$ or $R_2$ is —$CH_2CH_2$—$NR_aR_b$ wherein $R_a$ and $R_b$ together with the nitrogen to which they are attached form a piperazino, pyrrolidino, piperidino, morpholino, or thiomorpholino ring.
Another specific value for $R_1$ and $R_2$ together is =O.
Another specific value for $R_1$ and $R_2$ together is =S.
Another specific value for $R_1$ and $R_2$ together is =NH.
A preferred compound of formula (IV) is the compound 2,3-dimethoxy-13H-8,10,12-trioxa-5,6-diaza-cyclopenta[b]chrysene, 2,3-dimethoxy-13H-8,10,12-trioxa-6-aza-cyclopenta[b]chrysene, or a pharmaceutically acceptable salt thereof.

Certain compounds of formula (IV) can function as prodrugs for other compounds of formula (IV). For example, a compound of formula (IV) wherein Y and/or Z is —O—P(=O)(OH)$_2$, or —C(=O)$NR_cR_d$ can function as a prodrug for a corresponding compound of formula (IV) wherein Y and or Z is hydroxy. Accordingly, a specific sub set of compounds of formula (IV) are compounds wherein Y and/or Z is —O—P(=O)(OH)$_2$, or —O—C(=O)NR$_c$R$_d$. A particularly preferred compound is a compound of formula (IV) wherein Y and/or Z is —O—P(=O)(OH)$_2$. Another preferred compound is a compound of formula (IV) wherein Y and/or Z is —O—C(=O)NR$_c$R$_d$, wherein R$_c$ and/or R$_d$ is (C$_1$-C$_6$)alkyl substituted with one or more —NR$_e$R$_f$ wherein R$_e$ and R$_f$ are each independently (C$_1$-C$_6$)alkyl. Another preferred compound is a compound of formula (IV) wherein Y and/or Z is —O—C(=O)NR$_c$R$_d$, wherein R$_c$ and R$_d$ together with the nitrogen to which they are attached form a N'-(alkyl)piperazino, pyrrolidino, or piperidino ring. A more preferred compound is a compound of formula (IV) wherein Y and/or Z is —O—C(=O)NR$_c$R$^d$, wherein R$_c$ and R$_d$ together with the nitrogen to which they are attached form a piperidino ring, which ring is optionally substituted with an N-linked heterocycle (e.g. piperidino) ring. A compound of formula IV can be prepared by subjecting a corresponding intermediate of formula A to suitable cyclization conditions; for example, by treatment with palladium acetate and tri-o-tolylphosphine, as illustrated in Scheme 1 below. A compound of formula IV can also be prepared by subjecting a corresponding intermediate of formula B to conditions suitable for the formation of the ring system; for example by treatment with a suitable tin reagent, as illustrated in Scheme 2 below. Compounds of the present invention include intermediates of formulas A and B.

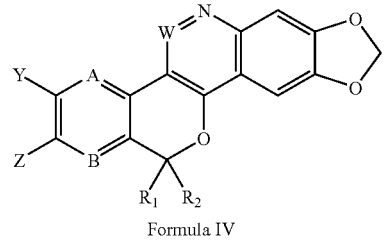

Formula IV

Other conditions suitable for formation of the ring system from intermediates of formula A and formula B are well known to the art. For example, see Feiser and Feiser, "Reagents for Organic Synthesis", Vol. 1, 1967; March, J. "Advanced Organic Chemistry", John Wiley & Sons, 4 ed. 1992; House, H. O., "Modern Synthetic Reactions", 2d ed., W. A. Benjamin, New York, 1972; and Larock, R. C., *Comprehensive Organic Transformations*, 2$^{nd}$ edition, 1999, Wiley-VCH Publishers, New York.

An intermediate of formula A can be prepared from readily available starting materials using procedures known in the art, or can be prepared procedures illustrated below.

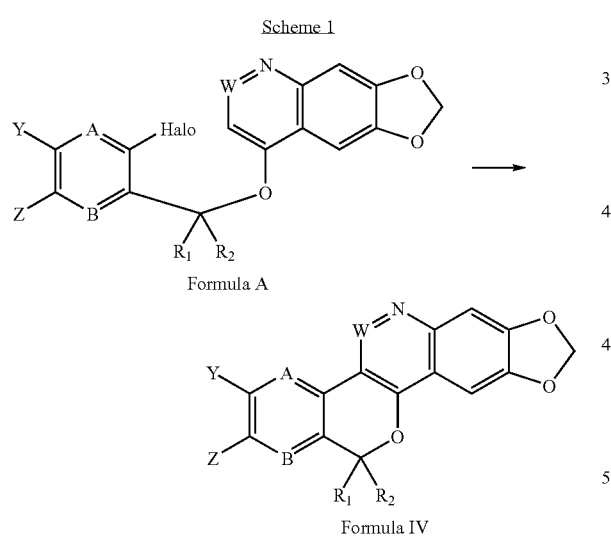

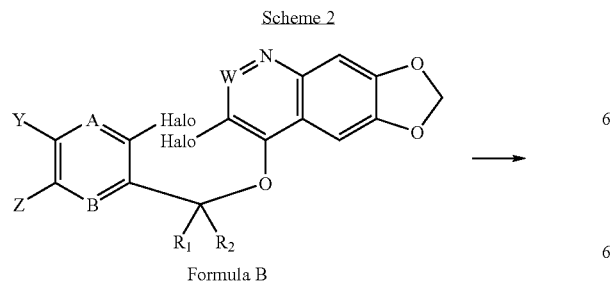

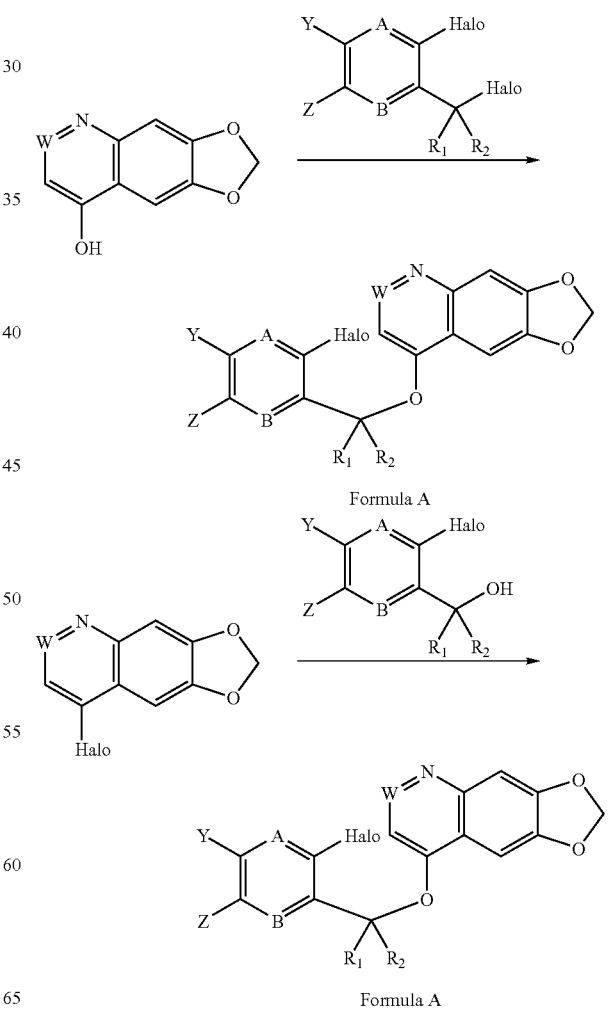

Similarly, an intermediate of formula B can be prepared from readily available starting materials using procedures known in the art, or can be prepared using procedures illustrated below.

Formula B

Formula B

Alternatively, one can modify compounds of formula IV to form desired derivatives related to formula IV as illustrated below.

Where R₂ is not H

Where R₁ is not H

Where X = S, NR₂

The Following Specific Values, Preferred Values and Discussion Relate to Compounds of Formula V.

Specifically, $(C_1-C_6)$alkyl can be methyl, ethyl, propyl, isopropyl, butyl, iso-butyl, sec-butyl, pentyl, 3-pentyl, or hexyl.

Specifically, $(C_1-C_6)$alkoxy can be methoxy, ethoxy, propoxy, isopropoxy, butoxy, iso-butoxy, sec-butoxy, pentoxy, 3-pentoxy, or hexoxy.

A specific compound of formula V is a compound of formula XXII:

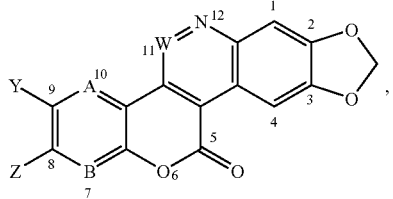

or a pharmaceutically acceptable salt thereof.

Another specific compound of formula V is a compound of formula XXIII:

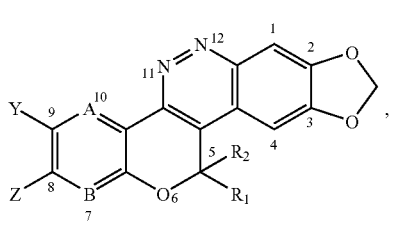

or a pharmaceutically acceptable salt thereof.
A specific value for W is N.
Another specific value for W is CH.
A specific value for A is CH.
Another specific value for A is N.
A specific value for B is N.
Another specific value for B is CH.
A specific value for Y is OH.
Another specific value for Y is $(C_1-C_6)$alkoxy.
Another specific value for Y is —$OCH_3$.
Another specific value for Y is substituted $(C_1-C_6)$alkoxy.
Another specific value for Y is —$OCH_2CH_2OH$.
Another specific value for Y is —$OCH_2CH_2OCH_2CH_3$.
Another specific value for Y is —O—$CH_2$—CHOH—$CH_2$—OH.
Another specific value for Y is —O—$CH_2CH_2$—$NR_aR_b$ wherein $R_a$ and $R_b$ are hydrogen or $(C_1-C_6)$alkyl.
Another specific value for Y is —O—$CH_2CH_2$—$NR_aR_b$ wherein $R_a$ and $R_b$ together with the nitrogen to which they are attached form a piperazino, pyrrolidino, piperidino, morpholino, or thiomorpholino ring.
Another specific value for Y is —O—C(=O)$CH_2$—$NR_aR_b$.
Another specific value for Y is —O—C(=O)—CHOH—$CH_2$—OH.
Another specific value for Y is $(C_1-C_6)$alkyl substituted with one or more tetrahydrofuranyl, tetrahydropyranyl, or 1,4-dioxanyl rings.
Another specific value for Y is —O—C(=O)$CH_2$—$NR_aR_b$.
A specific value for Z is OH.
Another specific value for Z is $(C_1-C_6)$alkoxy.
Another specific value for Z is $OCH_3$.
Another specific value for Z is substituted $(C_1-C_6)$alkoxy.
Another specific value for Z is —$OCH_2CH_2OH$.
Another specific value for Z is —$OCH_2CH_2OCH_2CH_3$.
Another specific value for Z is —O—$CH_2$—CHOH—$CH_2$—OH.
Another specific value for Z is —$OCH_2CH_2$—$NR_aR_b$ wherein $R_a$ and $R_b$ are hydrogen or $(C_1-C_6)$alkyl.
Another specific value for Z is —O—$CH_2CH_2$—$NR_aR_b$ wherein $R_a$ and $R_b$ together with the nitrogen to which they are attached form a piperazino, pyrrolidino, piperidino, morpholino, or thiomorpholino ring.
Another specific value for Z is —O—C(=O)—CHOH—$CH_2$—OH.
Another specific value for Z is $(C_1-C_6)$alkyl substituted with one or more tetrahydrofuranyl, tetrahydropyranyl, or 1,4-dioxanyl rings.
Another specific value for Z is —O—C(=O)$CH_2$—$NR_aR_b$.
A specific value for $R_1$ or $R_2$ is a $(C_1-C_6)$alkyl substituted with one or more hydroxy groups.
Another specific value for $R_1$ or $R_2$ is a $(C_1-C_6)$alkyl substituted with one hydroxy group.
Another specific value for $R_1$ or $R_2$ is a $(C_1-C_6)$alkyl substituted with one or more mercapto groups.
Another specific value for $R_1$ or $R_2$ is a $(C_1-C_6)$alkyl substituted with one mercapto group.
Another specific value for $R_1$ or $R_2$ is a $(C_1-C_6)$alkyl substituted with one or more carboxy groups.
Another specific value for $R_1$ or $R_2$ is a $(C_1-C_6)$alkyl substituted with one carboxy group.
Another specific value for $R_1$ or $R_2$ is a $(C_1-C_6)$alkyl substituted with one or more $NR_aR_b$ groups.
Another specific value for $R_1$ or $R_2$ is a $(C_1-C_6)$alkyl substituted with one $NR_aR_b$ group.
Another specific value for $R_1$ or $R_2$ is a $(C_1-C_6)$alkyl substituted with one or more $NH_2$ groups.
Another specific value for $R_1$ or $R_2$ is a $(C_1-C_6)$alkyl substituted with one $NH_2$ group.
Another specific value for $R_1$ or $R_2$ is a $(C_1-C_6)$alkyl substituted with one or more hydroxy, mercapto, carboxy, amino, piperazinyl, pyrrolidinyl, piperidinyl, morpholinyl, thiomorpholinyl, tetrahydrofuranyl, tetrahydropyranyl, or 1,4-dioxanyl groups.
Another specific value for $R_1$ or $R_2$ is a $(C_1-C_6)$alkyl with from 2 to 4 carbon atoms and substituted with one to two groups selected from hydroxy, mercapto, carboxy, amino, piperazinyl, pyrrolidinyl, piperidinyl, morpholinyl, thiomorpholinyl, tetrahydrofuranyl, tetrahydropyranyl, or 1,4-dioxanyl.
Another specific value for $R_1$ or $R_2$ is 2-hydroxymethyl.
Another specific value for $R_1$ or $R_2$ is 2-hydroxyethyl.
Another specific value for $R_1$ or $R_2$ is 3-hydroxypropyl.
Another specific value for $R_1$ or $R_2$ is 2-hydroxypropyl.
Another specific value for $R_1$ or $R_2$ is H.
Another specific value for $R_1$ or $R_2$ is —$CH_2$—CHOH—$CH_2$—OH.
Another specific value for $R_1$ or $R_2$ is —$CH_2CH_2$—$NR_aR_b$ wherein $R_a$ and $R_b$ are hydrogen or $(C_1-C_6)$alkyl.
Another specific value for $R_1$ or $R_2$ is —$CH_2CH_2$—$NR_aR_b$ wherein $R_a$ and $R_b$ together with the nitrogen to which they are attached form a piperazino, pyrrolidino, piperidino, morpholino, or thiomorpholino ring.
Another specific value for $R_1$ and $R_2$ together are =O.
Another specific value for $R_1$ and $R_2$ together are =S.
Another specific value for $R_1$ and $R_2$ together are =NH.
A preferred compound of formula (V) is the compound 2,3-dimethoxy-12H-8,10,13-trioxa-5,6-diaza-cyclopenta[b]chrysene, 2,3-dimethoxy-12H-8,10,13-trioxa-6-aza-cyclopenta[b]chrysene, or a pharmaceutically acceptable salt thereof.

Certain compounds of formula (V) can function as prodrugs for other compounds of formula (V). For example, a compound of formula (V) wherein Y and/or Z is —O—P(=O)(OH)$_2$, or —O—C(=O)$NR_cR_d$; can function as a prodrug for a corresponding compound of formula (V) wherein Y and or Z is hydroxy. Accordingly, a specific sub set of compounds of formula (V) are compounds wherein Y and/or Z is —O—P(=O)(OH)$_2$, or —O—C(=O)NR$_c$R$_d$. A particularly preferred compound is a compound of formula (V) wherein Y and/or Z is —O—P(=O)(OH)$_2$. Another preferred compound is a compound of formula (V) wherein Y and/or Z is —O—C(=O)NR$_c$R$_d$, wherein R$_c$ and/or R$_d$ is (C$_1$-C$_6$)alkyl substituted with one or more —NR$_e$R$_f$ wherein R$_e$ and R$_f$ are each independently (C$_1$-C$_6$)alkyl. Another preferred compound is a compound of formula (V) wherein Y and/or Z is —O—C(=O)NR$_c$R$_d$, wherein R$_c$ and R$_d$ together with the nitrogen to which they are attached form a N'-(alkyl)piperazino, pyrrolidino, or piperidino ring. A more preferred compound is a compound of formula (V) wherein Y and/or Z is —O—C(=O)NR$_c$R$_d$, wherein R$_c$ and R$_d$ together with the nitrogen to which they are attached form a piperidino ring, which ring is optionally substituted with an N-linked heterocycle (e.g. piperidino) ring. A compound of formula V can be prepared by subjecting a corresponding intermediate of formula A to suitable cyclization conditions; for example, by treatment with palladium acetate and tri-o-tolylphosphine, as illustrated in Scheme 1 below. A compound of formula V can also be prepared by subjecting a corresponding intermediate of formula B to conditions suitable for the formation of the ring system; for example by treatment with a suitable tin reagent, as illustrated in Scheme 2 below. Compounds of the present invention include intermediates of formulas A and B.

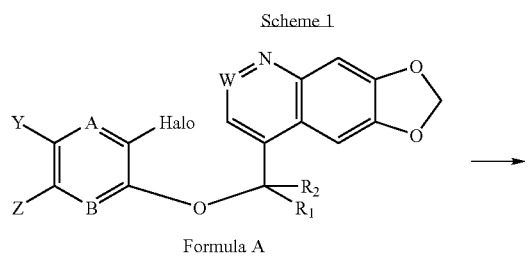

Scheme 1

Formula A

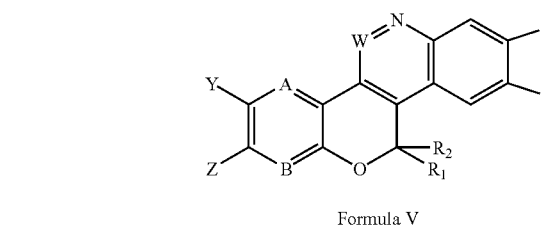

Scheme 2

Formula B

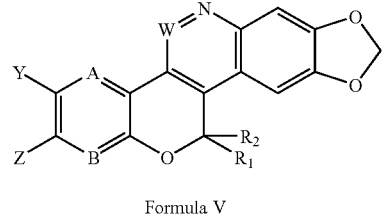

Formula V

Other conditions suitable for formation of the ring system from intermediates of formula A and formula B are well known to the art. For example, see Feiser and Feiser, "Reagents for Organic Synthesis", Vol. 1, 1967; March, J. "Advanced Organic Chemistry", John Wiley & Sons, 4 ed. 1992; House, H. O., "Modern Synthetic Reactions", 2d ed., W. A. Benjamin, New York, 1972; and Larock, R. C., Comprehensive Organic Transformations, 2$^{nd}$ edition, 1999, Wiley-VCH Publishers, New York.

An intermediate of formula A can be prepared from readily available starting materials using procedures known in the art, or can be prepared using at least two different procedures illustrated below.

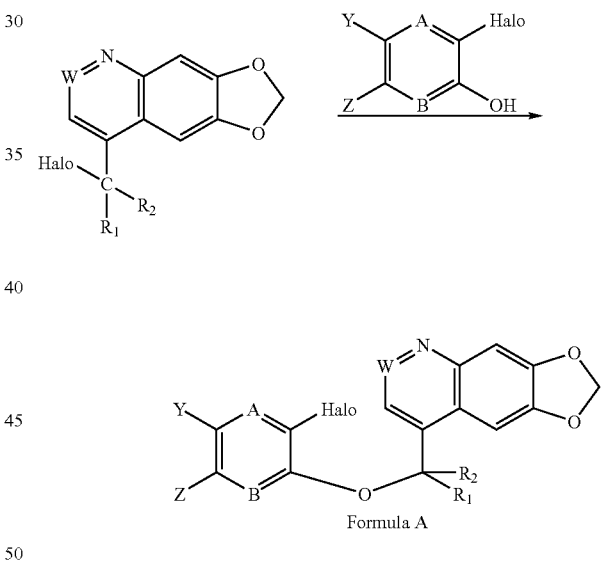

Formula A

Similarly, an intermediate of formula B can be prepared from readily available starting materials using procedures that are known in the art, or can be prepared using procedures illustrated below.

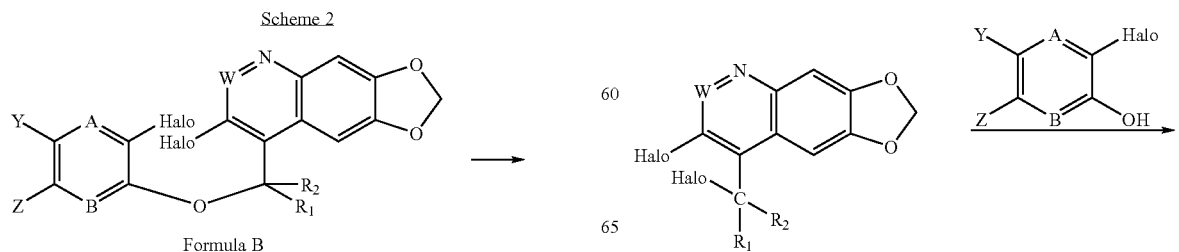

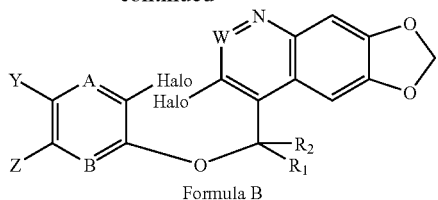

Formula B

Alternatively, one can modify these compounds to form the compounds of formula V as illustrated below.

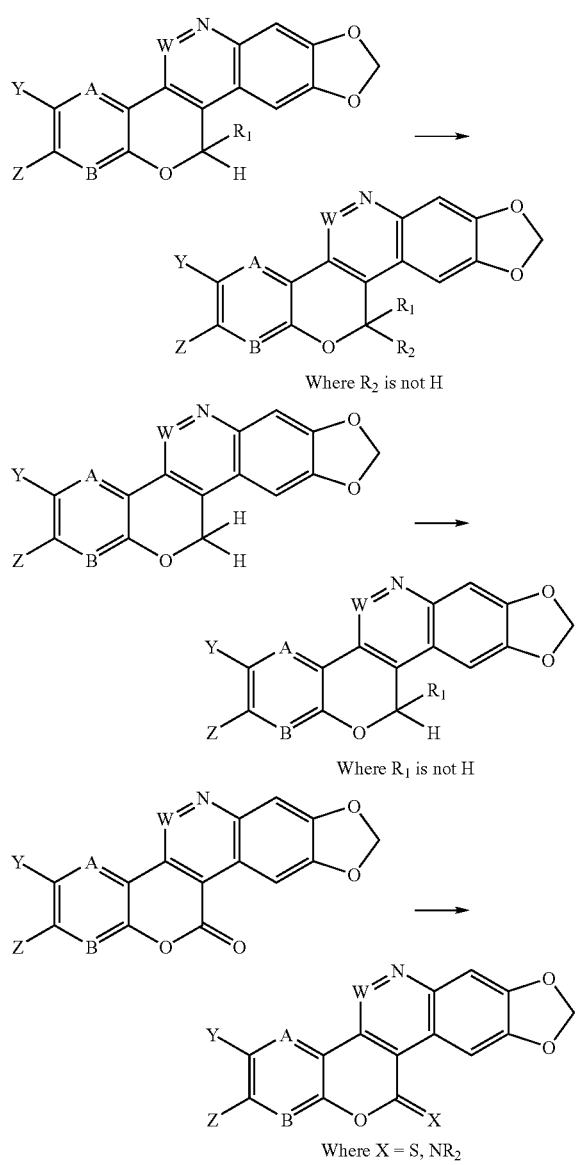

General Discussion

The starting materials employed in the synthetic methods described herein are commercially available, have been reported in the scientific literature, or can be prepared from readily available starting materials using procedures known in the field. It may be desirable to optionally use a protecting group during all or portions of the above described synthetic procedures. Such protecting groups and methods for their introduction and removal are well known in the art. See Greene, T. W.; Wutz, P. G. M. "Protecting Groups In Organic Synthesis" second edition, 1991, New York, John Wiley & Sons, Inc.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine topoisomerase inhibition activity or cytotoxic activity using the standard tests described herein, or using other similar tests which are well known in the art. Compounds of the present invention can contain chiral centers, for example, in any of the substituents Y, Z, and $R_1$.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal, for example, sodium, potassium or lithium, or alkaline earth metal, for example calcium, salts of carboxylic acids can also be made.

The compounds of the invention can be formulated as pharmaceutical compositions and administered to a mammalian host, such as a human patient in a variety of forms adapted to the chosen route of administration, that is, orally or parenterally, by intravenous, intramuscular, topical or subcutaneous routes.

Thus, the present compounds may be systemically administered, for example, orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound may conveniently be administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to effect topoisomerase I or II mediated DNA cleavage can be determined using pharmacological models that are well known to the art, for example, using a model like Test A described below.

Test A. Topoisomerase I-mediated DNA Cleavage Assay

Human topoisomerase I was expressed in *E. Coli* and isolated as a recombinant fusion protein using a T7 expression system as described previously, see Makhey, D. et al., *Bioorg. Med. Chem.*, 2000, 8, 1-11. DNA topoisomerase I was purified from calf thymus gland as reported previously, see Maniatis, T., et al., J. Molecular Cloning, a Laboratory Manual, Cold Spring Harbor Laboratory, Cold Spring Harbor, N.Y., 149-185). Plasmid YepG was also purified by the alkali lysis method followed by phenol deproteination and CsCl/ethidium isopycnic centrifugation method as described, see Maniatis, T.; Fritsch, E. F.; Sambrook, J. *Molecular Cloning, a Laboratory Manual*; Cold Spring Harbor Laboratory: Cold Spring Harbor, N.Y. 1982; pp 149-185. The end-labeling of the plasmid was accomplished by digestion with a restriction enzyme followed by end-filling with Klenow polymerase as previously described, see Liu, L. F.; Rowe, T. C.; Yang, L.; Tewey, K. M.; Chen, G. L., *J. Biol. Chem.* 1983, 258, 15365. Cleavage assays were performed as previously reported, see B. Gatto et al. *Cancer Res.*, 1996, 56, 2795-2800. The drug and the DNA in presence of topoisomerase I was incubated for 30 minutes at 37° C. After development of the gels, typically 24-hour exposure was used to obtain autoradiograms outlining the extent of DNA fragmentation. Topoisomerase I-mediated DNA cleavage values are reported as REC, Relative Effective Concentration, i.e. concentrations relative to 2,3-dimethoxy-8,9-methylenedioxybenzo[i]phenanthridine, whose value is arbitrarily assumed as 1.0, that are able to produce the same cleavage on the plasmid DNA in the presence of human topoisomerase I. Relative potency was based upon the relative amount of drug needed to induce approximately 10% DNA fragmentation. Assays are performed under the direction of Dr. L. F. Liu, Department of Pharmacology, The University of Medicine and Dentistry of New Jersey, Robert Wood Johnson Medical School, Piscataway, N.J.

A similar assay can be used to evaluate the ability of a compound of the invention to effect topoisomerase II mediated DNA cleavage, by replacing the human topoisomerase I used in Test A with a suitable topoisomerase II.

The cytotoxic effects of a compound of the invention can be determined using pharmacological models that are well known to the art, for example, using a model like Test B described below.

Test B. Inhibition of Cell Growth: MTT-Microtiter Plate Tetrazolinium Cytotoxicity Assay (RPMI 8402, CPT-K5, U937, U937/CR Cells)

The cytotoxicity is determined using the MTT-microtiter plate tetrazolinium cytotoxicity assay (MTA), see Chen A. Y. et al. *Cancer Res.* 1993, 53, 1332; Mosmann, T. J., J. *Immunol. Methods* 1983, 65, 55; and Carmichael, J. et al. *Cancer Res.* 1987, 47, 936. The human lymphoblast RPMI 8402 and its camptothecin-resistant variant cell line, CPT-K5 were provided by Dr. Toshiwo Andoh (Anchi Cancer Research Institute, Nagoya, Japan), see Andoh, T.; Okada, K, *Adv. in Pharmacology* 1994, 29B, 93. Human U-937 myeloid leukemia cells and U-937/CR cells were described by Rubin et al., *J. Biol. Chem.*, 1994, 269, 2433-2439. The cytotoxicity assay is performed by using 96-well microtiter plates using 2000 cells/well, in 200 mL of growth medium. Cells are grown in suspension at 37° C. in 5% $CO_2$ and maintained by regular passage in RPMI medium supplemented with 10% heat-inactivated fetal bovine serum, L-glutamine (2 mM), penicillin (100 U/mL), and streptomycin (0.1 mg/mL). For determination of $IC_{50}$, cells are exposed continuously for 3-4 days to varying concentrations of drug, and MTT assays were performed at the end of the fourth day. Each assay is performed with a control that did not contain any drug. All assays are performed at least twice in 6 replicate wells. All assays are performed under the direction of Dr. L. F. Liu, Department of Pharmacology, The University of Medicine and Dentistry of New Jersey, Robert Wood Johnson Medical School, Piscataway, N.J.

The compounds of the invention can function as cytotoxic agents against tumor cell lines, including multi-drug resistant tumor cell lines. Thus, the compounds are useful to treat cancer and can be used to treat tumors that are resistant to other specific chemotherapeutic agents.

Topoisomerase inhibitors are also known to possess antibacterial, antifungal, antipsoritic (psoriasis), antiprotozoal, antihelmetic, and antiviral activity. Accordingly, the topoisomerase inhibitors of the invention may also be useful as antibacterial, antifungal, antipsoritic (psoriasis), antiprotozoal, antihelmetic, or antiviral agents. In particular, compounds of the invention that demonstrate little or no activity as mammalian topoisomerase I poisons, because of the possibility of similar molecular mechanism of action, could be highly active and selective antibacterial, antifungal, antipsoritic (psoriasis), antiprotozoal, antihelmetic, or antiviral agents. Thus, certain compounds of the invention may be particularly useful as systemic antibacterial, antifungal, antipsoritic (psoriasis), antiprotozoal, antihelmetic, or antiviral agents in mammals. The invention also provides the use of a compound of the invention for the manufacture of a medicament useful for producing an antibacterial, antifungal, antipsoritic (psoriasis), antiprotozoal, antihelmetic, or antiviral effect in a mammal.

As used herein, the term "solid mammalian tumors" include cancers of the head and neck, lung, mesothelioma, mediastinum, esophagus, stomach, pancreas, hepatobiliary system, small intestine, colon, rectum, anus, kidney, ureter, bladder, prostate, urethra, penis, testis, gynecological organs, ovarian, breast, endocrine system, skin central nervous system; sarcomas of the soft tissue and bone; and melanoma of cutaneous and intraocular origin. The term "hematological malignancies" includes childhood leukemia and lymphomas, Hodgkin's disease, lymphomas of lymphocytic and cutaneous origin, acute and chronic leukemia, plasma cell neoplasm and cancers associated with AIDS. The preferred mammalian species for treatment are humans and domesticated animals.

The invention will now be illustrated by the following non-limiting Examples. Specific compounds of the present invention can be prepared as illustrated in the following schemes using known reactions and reagents.

EXAMPLE 1
Preparation of Representative Compounds of Formula I
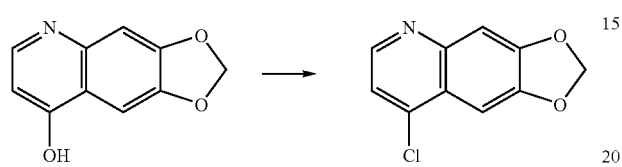
Phenol; CH₃CH₂NH₂
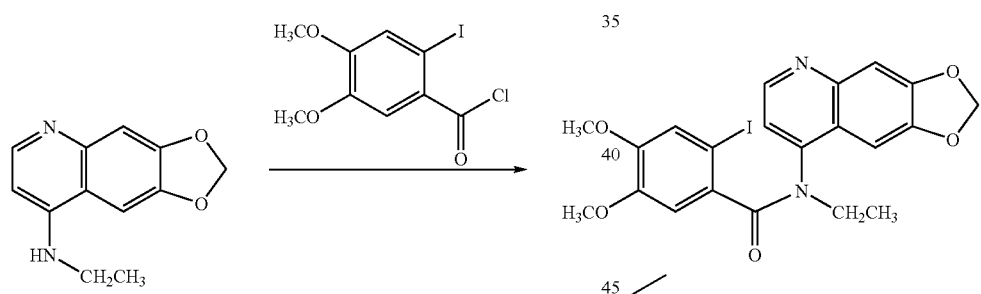
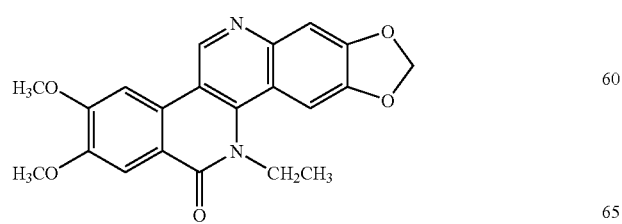

EXAMPLE 2
Preparation of Representative Compounds of Formula I
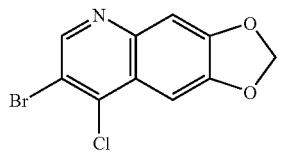
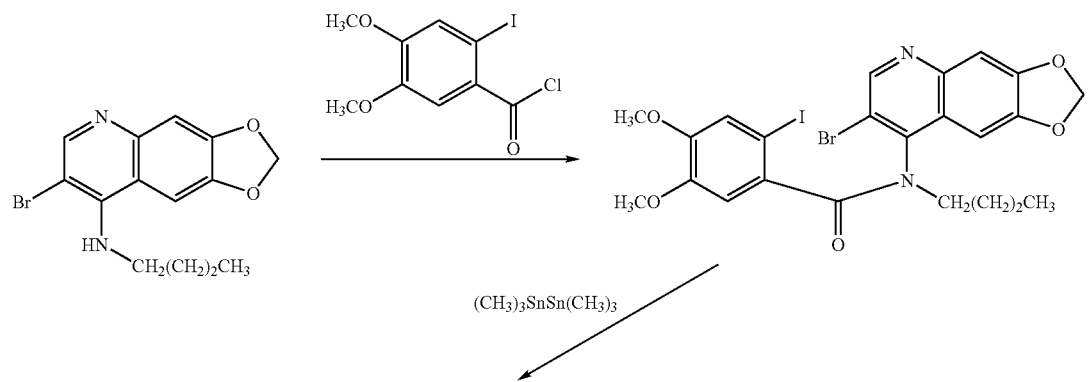
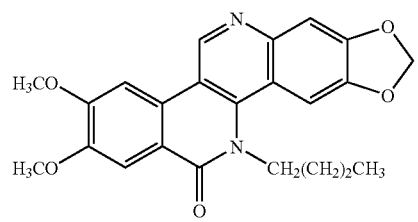
Specific compounds of the present invention can be prepared in accordance with the following schemes using known reactions and reagents.

EXAMPLE 3
Preparation of Representative Compounds of Formula II
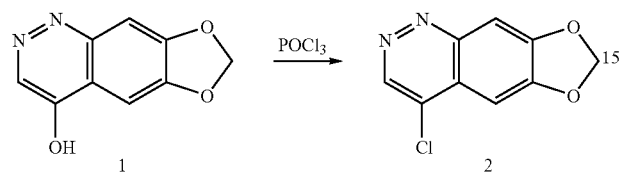
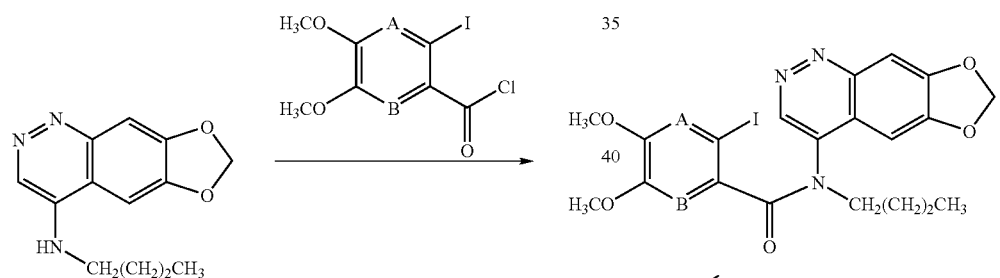
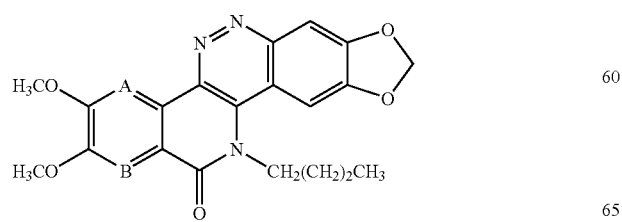

EXAMPLE 4
Preparation of Representative Compounds of Formula II
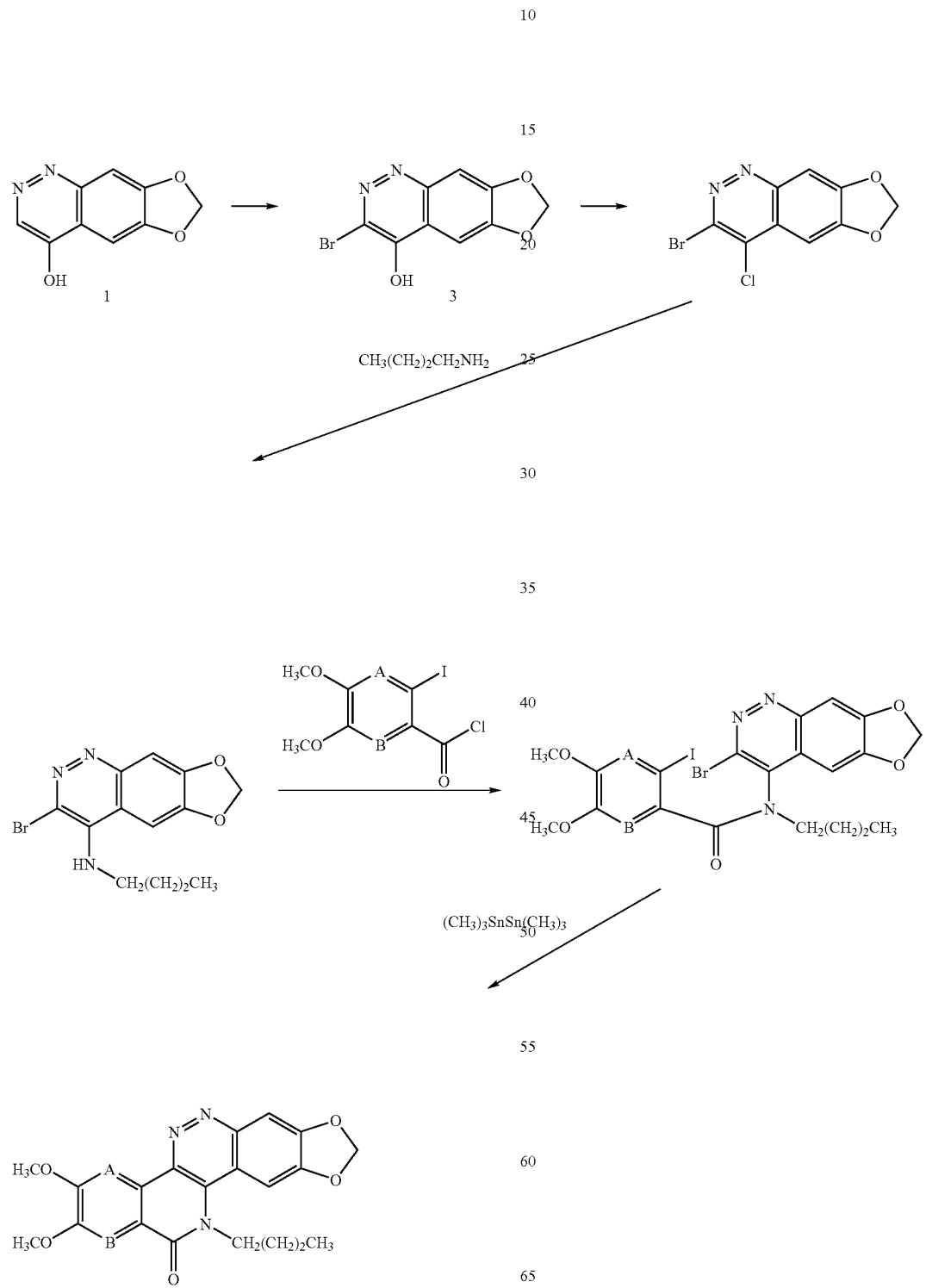

EXAMPLE 5
Preparation of Representative Compounds of Formula III
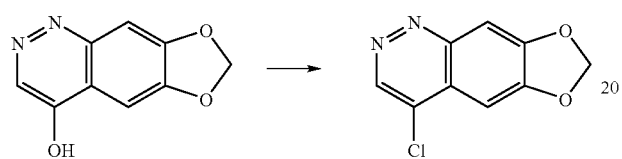
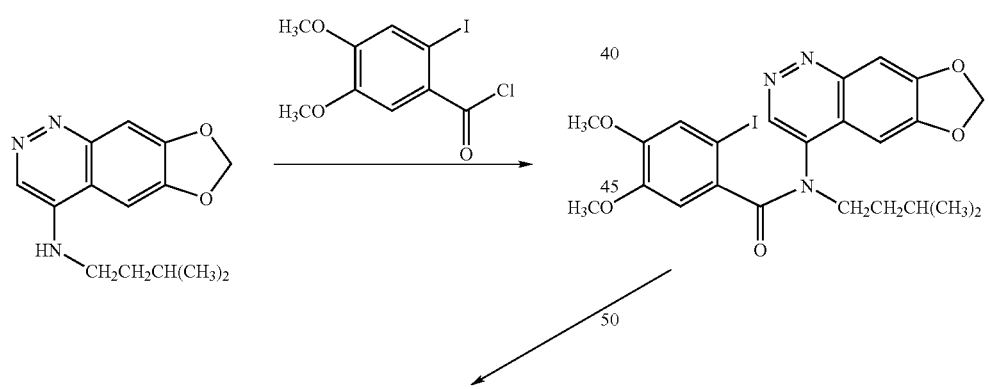
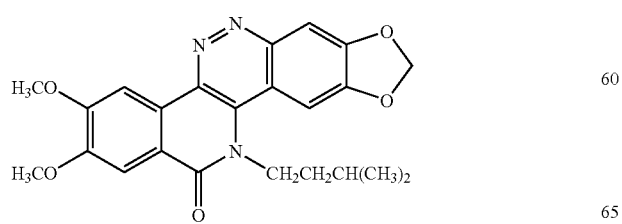

EXAMPLE 6
Preparation of Representative Compounds of Formula III
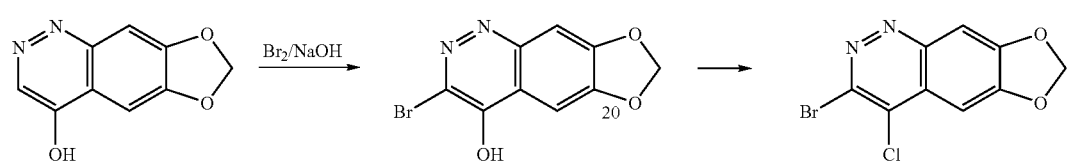
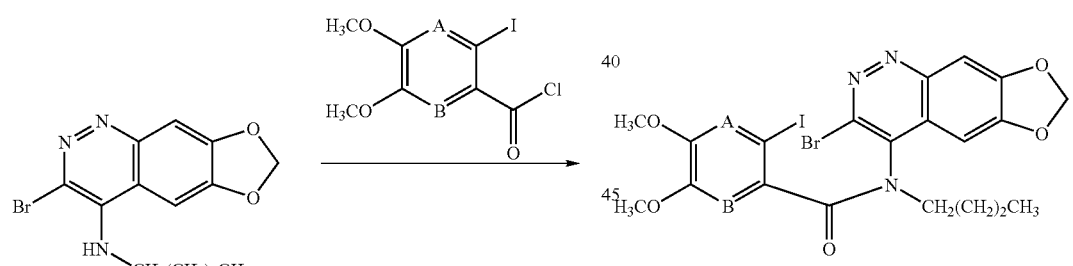
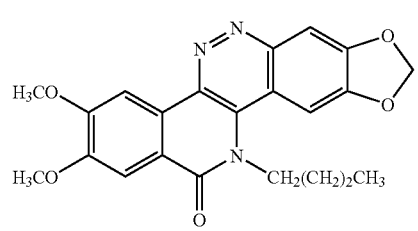

US 7,319,105 B2
EXAMPLE 7
Preparation of Representative Compounds of Formula IV
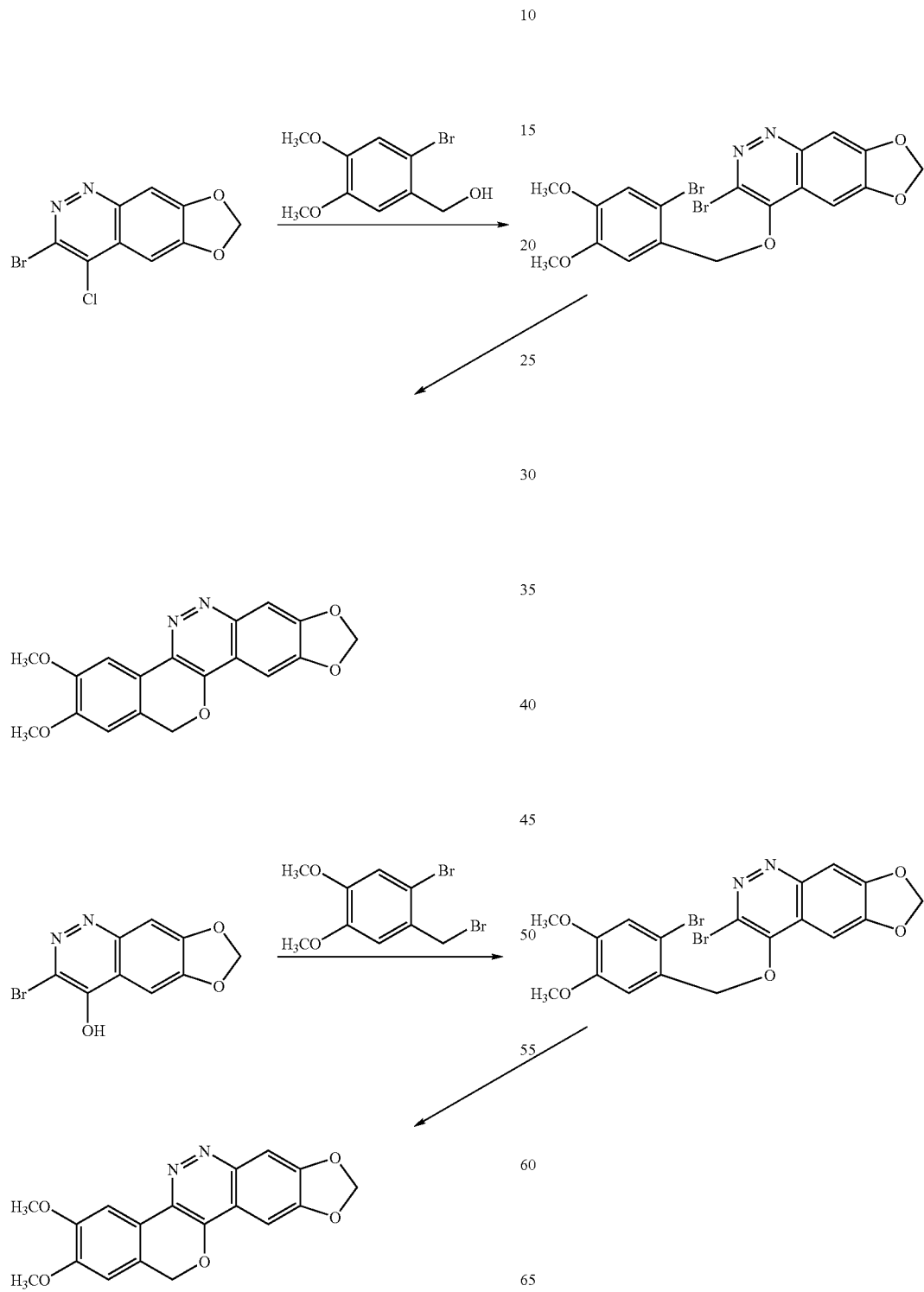

EXAMPLE 8

Preparation of a Representative Compound of Formula V

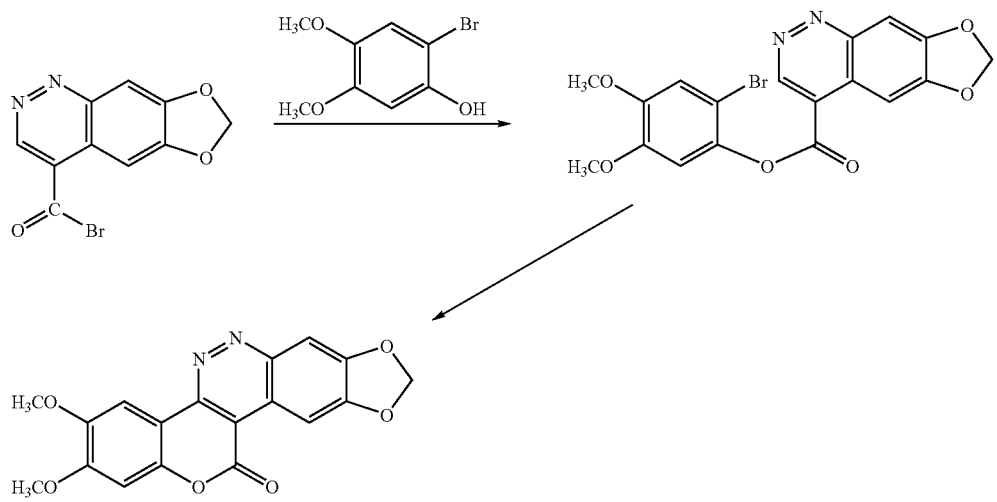

EXAMPLE 9

Preparation of a Representative Compound of Formula V

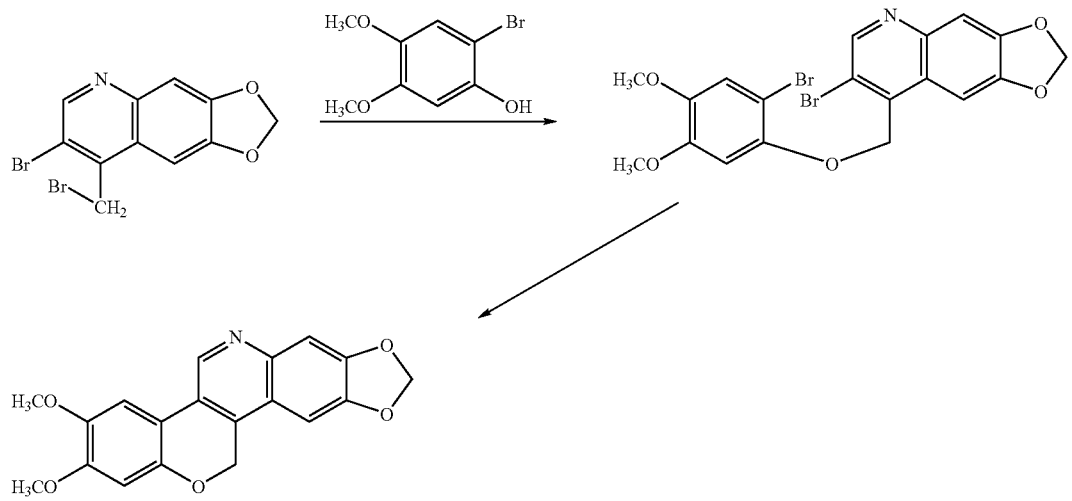

EXAMPLE 10

Synthesis of 2,3-Dimethoxy-8,9-methylenedioxy-11-(n-butyl)-11H-5,6,11-triazachrysen-12-one A mixture of N-(6,7-Methylenedioxycinnolin-4-yl)-N-(n-butyl)-2-iodo-4,5-dimethoxybenzamide (1.0 mmol equiv.), Pd(OAc)$_2$ (0.2 mmol equiv.), P(o-tolyl)$_3$ (0.4 mmol equiv.), and Ag$_2$CO$_3$ (2.0 mmol equiv) was heated to reflux in DMF (30 mL per mmol equiv.) with stirring. The reaction mixture was allowed to cool to room temperature, diluted with CHCl$_3$, and filtered through Celite. The sicciate was extensively washed with 10% CH$_3$OH in CHCl$_3$. The filtrate was concentrated in vacuo and the residue chromatographed on silica gel using chloroform:methanol to provide the title compound (123 mg, 0.2 mmol) in 27% yield with a reaction time 90 min; mp 299° C.; IR (KBr) 1654; $^1$H NMR (CDCl$_3$) δ 1.06 (t, 3H, J=7.4), 1.56 (m, 2H), 2.13 (m, 2H), 4.09 (s, 3H), 4.17 (s, 3H), 4.49 (m, 2H), 6.26 (s, 2H), 7.62 (s, 1H), 7.85 (s, 1H), 7.87 (s, 1H), 8.65 (s, 1H); $^{13}$C NMR (CDCl$_3$) δ 13.8, 20.2, 31.1, 48.6, 56.3, 56.6, 98.8, 102.7, 104.2, 106.5, 107.9, 119.7, 149.1, 150.1, 150.9, 151.4, 153.6, 154.2, 162.9; HRMS calcd for C$_{22}$H$_{21}$N$_3$O$_5$H: 408.1559. Found 408.1543.

The intermediate compound N-(6,7-Methylenedioxycinnolin-4-yl)-N-(n-butyl)-2-iodo-4,5-dimethoxybenzamide was prepared as follows.

a. 6,7-Methylenedioxy-4-cinnolone. A mixture of 6'-amino-3',4'-methylenedioxyacetophenone (2.4 g, 13.4 mmol) in concentrated hydrochloric acid (92 mL) and water (13 mL) was cooled to −5° C. and a diazotized by the dropwise addition of a solution of sodium nitrite (0.925 g, 13.4 mmol) in water (4 mL). After stirring for an additional hour at −5° C. the mixture was transferred to a bath preheated at 75° C. and left to stir at this temperature overnight. The reaction mixture was cooled to 5° C. to induce crystallization. This material was filtered and then added to 10% aqueous NaOH (100 mL), which was again filtered and dried under vacuum to yield 2.37 g of the cinnoline as a colorless solid, in 93% yield; mp 318-320° C.; $^1$H NMR (DMSO-$d_6$) δ 6.21 (s, 2H), 6.97 (s, 1H), 7.30 (s, 1H), 7.63 (s, 1H); $^{13}$C NMR (DMSO-$d_6$) δ 94.9, 100.3, 103.3, 120.1, 139.7, 139.9, 147.4, 153.5, 169.4; HRMS calcd for $C_9H_6O_3N_2$: 190.0378. Found: 190.0372.

b. 4-Chloro-6,7-methylenedioxycinnoline. 6,7-Methylenedioxy-4-cinnolone (1.0 g, 5.3 mmol) was added in small portions to a stirred mixture of phosphorus pentachloride (1.4 g, 6.7 mmol) and phosporus oxychloride (4 mL, 6.6 mmol) at room temperature. The reaction flask was heated to 80° C. for 4 hours, then cooled to room temperature and poured onto 50 g of crushed ice. Following neutralization of the solution with solid sodium acetate, the precipitate was removed by filtration and recrystallized from ethanol to give 800 mg of the chlorocinnoline as an off-white solid, in 73% yield; mp 203.5-204.5° C.; $^1$H NMR (CDCl$_3$) δ 6.25 (s, 2H), 7.39 (s, 1H), 7.73 (s, 1H), 9.14 (s, 1H); $^{13}$C NMR (CDCl$_3$) δ 97.8, 102.9, 105.1, 124.2, 133.4, 144.0, 150.0, 152.3, 152.7; HRMS calcd for $C_9H_5O_2N_2Cl$: 208.0040. Found: 208.0042.

c. N-(6,7-Methylenedioxycinnolin-4-yl)-n-butylamine. Butyl amine ((25 ml)) was added with stirring to 4-chloro-6,7-methylenedioxycinnoline (1 g, 4.7 mmol) and copper powder (250 mg). The reaction was then allowed to stir for 18 h at 80° C., and the solvent was removed under reduced pressure. The residue was partitioned between CHCl$_3$ and 10% NaOH. The aqueous layer was repeatedly separated with CHCl$_3$. All of the CHCl$_3$ solutions (initial partition and extracts) were combined and dried (MgSO$_4$) to provide the product in 32.5% yield; mp 247-248° C.; $^1$H NMR (CDCl$_3$) δ 1.02 (t, 3H, J=7.4), 1.50 (m, 2H), 1.73 (m, 2H), 3.40 (m, 2H), 4.59 (s, 1H), 6.14 (s, 2H), 6.96 (s, 1H), 7.57 (s, 1H), 8.59 (s, 1H); $^{13}$C NMR (CDCl$_3$) δ 13.8; 20.2, 29.7, 31.3, 42.8, 94.2, 102.1, 105.3, 112.7, 126.7, 140.6, 149.6, 150.7; HRMS calcd for $C_{13}H_{15}N_3O_2H$: 246.1243. Found 246.1237.

d. N-(6,7-Methylenedioxycinnolin-4-yl)-N-(n-butyl)-2-iodo-4,5-dimethoxybenzamide. A 2.0M solution of oxalyl chloride in CH$_2$Cl$_2$ (1.3 equiv.) was added to a solution of 2-iodo-4,5-dimethoxybenzoic acid (1.0 equiv.) in anhydrous CH$_2$Cl$_2$ (≈60 mL per 10 mmol benzoic acid) and the solution stirred at reflux for 3 h. The mixture was allowed to cool and was then concentrated to dryness in vacuo. To the residues was added a solution of appropriate N-(6,7-methylenedioxy-cinnolin-4-yl)-n-butylamine (1.0 equiv), triethylamine (2 equiv.) in CH$_2$Cl$_2$ (≈60 mL per 4 mmol aminoquinoline). The reaction mixture was then stirred at reflux under N$_2$. The reaction mixture was cooled and washed with sat. NaHCO$_3$ and extracted with 3% HCl. The aqueous layer was neutralized with 20% NaOH and extracted with CHCl$_3$, dried (MgSO$_4$) and evaporated to provide the product (350 mg, 1.4 mmol); in 19% yield with a reaction time 18 h at 50° C. from the acid chloride prepared using 5.0 mmol of oxalyl chloride and 2.1 mmol of 2-iodo-4,5-dimethoxybenzoic acid; mp 133-134° C.; IR (KBr) 1654; $^1$H NMR (CDCl$_3$) δ 0.87 (t, 3H, J=7.2), 1.20-1.90 (m, 4H), 3.33 (s, 3H), 3.68 (s, 3H), 3.90 (m, 1H), 4.35 (m, 1H), 6.19 (d, 2H, J=3.2), 6.34 (s, 1H), 6.98 (s, 1H), 7.25 (s, 1H), 7.62 (s, 1H), 9.01 (s, 1H); $^{13}$C NMR (CDCl$_3$) δ 13.7, 20.1, 30.0, 49.4, 55.7, 56.1, 82.9, 96.5, 102.9, 105.6, 110.5, 121.9, 133.1, 148.3, 150.0, 151.8, 152.5, 169.7; HRMS calcd for $C_{22}H_{22}IN_3O_5Li$ 542.0764. Found 542.0757.

EXAMPLE 11

Synthesis of 8,9-Dimethoxy-2,3-methylenedioxy-5-(butyl)-5H-dibenzo[c,h]1,6-naphthyridin-6-one A mixture of the N-(6,7-Methylenedioxyquinolin-4-yl)-N-(butyl)-2-iodo-4,5-dimethoxybenzamide (1.0 mmol equiv.), Pd(OAc)$_2$ (0.2 mmol equiv.), P(o-tolyl)$_3$ (0.4 mmol equiv.), and Ag$_2$CO$_3$ (2.0 mmol equiv) was heated to reflux in DMF (30 mL per mmol equiv.) with stirring. The reaction mixture was allowed to cool to room temperature, diluted with CHCl$_3$, and filtered through Celite. The sicciate was extensively washed with 10% CH$_3$OH in CHCl$_3$. The filtrate was concentrated in vacuo and the residue chromatographed on silica gel using chloroform:methanol to provide the title compound; (24% yield); reaction time 45 min; mp 224° C. (dec.); IR (KBr) 1654; $^1$H NMR (CDCl$_3$); δ 0.99 (t, 3H, J=7.4), 1.62 (m, 2H), 2.09 (m, 2H), 4.07 (s, 3H), 4.14 (s, 3H), 4.49 (m, 2H), 6.19 (s, 2H), 7.50 (s, 1H), 7.61 (s, 1H), 7.70 (s, 1H), 7.92 (s, 1H), 9.40 (s, 1H); $^{13}$C NMR (CDCl$_3$) δ 13.7, 20.2, 31.2, 50.6, 56.3, 56.4, 100.7, 102.0, 102.2, 107.4, 108.8, 111.7, 114.9, 119.5, 127.4, 141.1, 143.7, 147.1, 147.5, 149.8, 150.3, 154.1, 164.0; HRMS calcd for $C_{23}H_{22}N_2O_5H$: 406.1529. Found 406.1534.

The intermediate N-(6,7-methylenedioxyquinolin-4-yl)-N-(butyl)-2-iodo-4,5-dimethoxybenzamide was prepared as follows.

a. 4-Chloro-6,7-methylenedioxyquinoline. Was prepared from 4-hydroxy-6,7-methylenedioxyquinoline using methods as previous described in the literature for the conversion of 4-hydroxyquinoline to 4-chloroquinoline. Compound 5 had: mp 127.5-128° C. (Lit.[28] mp 129° C.); $^1$H NMR (CDCl$_3$) 6.15 (s, 2H), 7.35 (d, 1H, J=4.7), 7.39 (s, 1H), 7.49 (s, 1H), 8.56 (d, 1H, J=4.7); $^{13}$C NMR (CDCl$_3$) 99.8, 102.2, 106.1, 119.9, 123.7, 129.8, 141.2, 147.7, 149.1, 151.4.

b. N-(6,7-Methylenedioxyquinolin-4-yl)butylamine. 4-Chloro-6,7-methylenedioxyquinoline was stirred in refluxing phenol (5.5 mol equiv.) for 2.5 h. The temperature was lowered to 100° C. and butylamine (1.0 mol equiv.) was added with stirring. The reaction was then allowed to stir at 100° C. for several hours, and the phenol removed by Kugelrohr distillation under reduced pressure. The residue was partitioned between CHCl$_3$ and 10% NaOH. The aqueous layer was repeatedly separated with CHCl$_3$. All of the CHCl$_3$ solutions (initial partition and extracts) were combined and dried (MgSO$_4$), and purified by column chromatography to provide the product; mp 186-187° C.; $^1$H NMR (CD$_3$OD) δ 1.02 (t, 3H, J=7.2), 1.52 (q, 2H, J=7.2), 1.75 (q, 2H J=7.2), 3.33 (q, 2H, J=7.2), 4.88 (b, 1H), 6.08 (s, 2H), 6.40 (d, 1H, J=5.6), 7.07 (s, 1H), 7.35 (s, 1H), 8.37 (d, 1H, J=6.0); $^{13}$C NMR (CH$_3$OD) δ 12.2, 19.3, 29.6, 42.3, 96.9, 97.3, 98.8, 102.3, 112.5, 138.7, 141.5, 147.3, 151.6, 152.8; HRMS calcd for $C_{14}H_{16}N_2O_2$: 244.1212. Found 244.1222.

c. N-(6,7-Methylenedioxyquinolin-4-yl)-N-(butyl)-2-iodo-4,5-dimethoxybenzamide.

A 2.0M solution of oxalyl chloride in $CH_2Cl_2$ (8.2 mmol) was added to a solution of 2-iodo-5,6-dimethoxybenzoic acid (1.9 mmol) in anhydrous $CH_2Cl_2$ (≈60 mL per 10 mmol benzoic acid) and the solution stirred at reflux for 3 h. The mixture was allowed to cool and was then concentrated to dryness in vacuo. To the residue was added a solution of N-(6,7-Methylenedioxyquinolin-4-yl)butylamine (400 mg, 1.6 mmol), triethylamine (2 equiv.) in $CH_2Cl_2$ (≈60 mL per 4 mmol aminoquinoline). The reaction mixture was then stirred at reflux under $N_2$ for 72 h. The residue was partitioned between $CHCl_3$ and 10% NaOH. The aqueous layer was repeatedly separated with $CHCl_3$. All of the $CHCl_3$ solutions (initial partition and extracts) were combined and dried ($MgSO_4$). The aqueous layer was neutralized with 20% NaOH and extracted with $CHCl_3$, dried ($MgSO_4$) and evaporated to provide the compound: $^1$H NMR ($CDCl_3$) δ 0.85 (t, 3H, J=7.4), 1.20-1.91 (m, 4H), 3.22 (s, 3H), 3.65 (s, 3H), 4.45 (m, 2H), 6.08 (d, 2H, J=1.8), 6.31 (s, 1H), 6.97 (s, 1H), 7.17 (d, 1H, J=4.8), 7.29 (s, 1H), 7.30 (s, 1H), 8.49 (d, 1H, J=4.8).

EXAMPLE 12

8,9-Dimethoxy-2,3-methylenedioxy-6H-5-oxa-12-aza-chrysene

A mixture of 4-(2-Iodo-4,5-dimethoxybenzyloxy)-6,7-methylenedioxyquinoline (186 mg, 0.4 mmol), $Pd(OAc)_2$ (18 mg, 0.08 mmol), P(o-tolyl)$_3$ (49 mg, 0.16 mmol), and silver carbonate (220 mg, 0.8 mmol) was heated to reflux in DMF (12 mL) and stirred under nitrogen for 25 minutes. The reaction mixture was cooled to room temperature, diluted with chloroform and filtered though a bed of Celite. The filter was washed well with 90:10 chloroform-methanol. Then the solvent was removed under reduced pressure and the resulting residue was chromatographed on silica gel using chloroform to give the cyclized compound (30 mg) as a faintly pink solid, in 23% yield; mp 239-242° C. (dec.); IR ($CHCl_3$) 3025, 3009, 2960, 2928, 2855, 1603, 1526, 1496, 1463, 1346, 1285, 1260, 1243, 1219, 1210, 1181, 1165, 1141, 1041; UV (THF) $\lambda_{max}$=222, 254, 282, 303, 326 (log ε=3.98, 4.16, 4.22, 4.12, 4.14); $^1$H NMR ($CDCl_3$) δ 3.95 (s, 3H), 4.01 (s, 3H), 5.33 (s, 2H), 6.11 (s, 2H), 6.71 (s, 1H), 7.30 (s, 1H), 7.34 (s, 1H), 7.42 (s, 1H), 8.95 (s, 1H); $^{13}$C NMR ($CDCl_3$) δ 56.3, 56.4, 68.9, 97.6, 101.7, 106.0, 108.4, 112.6, 116.6, 120.9, 122.2, 143.4, 147.2, 147.8, 149.4, 149.8, 150.9, 155.7; HRMS calcd for $C_{19}H_{15}NO_5$: 337.0950. Found: 337.0945.

The intermediate compound 4-(2-iodo-4,5-dimethoxybenzyloxy)-6,7-methylenedioxyquinoline was prepared as follows.

a. Diethyl 3,4-methylenedioxyanilinomethylene malonate. 3,4-methylenedioxyaniline (41.0 g, 0.3 mmol) and diethyl ethoxymethylenemalonate (64.8 g, 0.3 mmol) were refluxed in benzene for 3.5 hours. The solvent was evaporated in vacuo and the residue was washed with petroleum ether to give 88.3 g as a shiny grey-brown solid, in 96% yield; mp 99.5-101.0° C. (lit.[221] mp 102° C.); $^1$H NMR ($CDCl_3$) δ 1.34 (t, 3H, J=7.0), 1.40 (t, 3H, J=7.0) 4.25 (q, 2H, J=7.0), 4.31 (q, 2H, J=7.0), 6.01 (s, 2H), 6.60 (dd, 1H, J=8.5, J=2.2), 6.71 (d, 1H, J=2.2), 6.81 (d, 1H, J=8.5), 8.41 (d, 1H, J=14.0); $^{13}$C NMR ($CDCl_3$) δ 14.4, 14.6, 60.1, 60.4, 92.9, 99.4, 101.8, 108.9, 110.9, 134.3, 145.3, 148.9, 152.6, 165.8, 169.3.

b. 4-Hydroxy-6,7-methylenedioxy-3-quinolinecarboxylic acid ethyl ester. Diethyl 3,4-methylenedioxyanilinomethylene malonate (80.0 g, 0.261 mol) was stirred in polyphosphate ester (PPE) (250 g, 0.528 mol) at 120° C. with a mechanical stirrer for 2 hours. The reaction mixture was poured into ice water (700 mL) and stirred until homogenous. The mixture was then neutralized (pH 8) with ammonium hydroxide, and the precipitate was filtered, washed well with water, and dried to give 54.7 g as a brown solid, in 80% yield; mp 277-278° C.; $^1$H NMR (DMSO-$d_6$) δ 1.26 (t, 3H, J=7.0), 4.16 (q, 2H, J=7.0), 6.09 (s, 2H), 7.02 (s, 1H), 7.38 (s, 1H), 8.48 (s, 1H).

c. 4-Hydroxy-6,7-methylenedioxy-3-quinolinecarboxylic acid. 4-Hydroxy-6,7-methylenedioxy-3-quinolinecarboxylic acid ethyl ester (45.0 g, 0.172 mol) was added to a solution of KOH (16.8 g, 0.258 mol) in ethanol (500 mL) and the mixture was heated to reflux with stirring for 20 hours. The reaction flask was then cooled and ethanol was evaporated under reduced pressure. Then 800 mL of water were added with stirring to fully dissolve the potassium salt, and the solution was filtered to remove any impurities. Concentrated HCl was added to bring the mixture to pH 1, and the free acid was filtered off and dried under vacuum, to give 33.9 g as a beige solid, in 84%; mp>300° C. (lit.[221] mp>290° C.); $^1$H NMR (DMSO-$d_6$) δ 6.27 (s, 2H), 7.30 (s, 1H), 7.55 (s, 1H), 8.72 (s, 1H); $^{13}$C NMR (DMSO-$d_6$) δ 98.5, 101.8, 103.8, 107.9, 120.8, 137.9, 143.5, 148.1, 153.7, 167.4, 177.4.

d. 6,7-Methylenedioxy-4-quinolone. A suspension of 4-Hydroxy-6,7-methylenedioxy-3-quinolinecarboxylic acid (30 g, 0.129 mol) in diphenyl ether (320 mL) was heated to reflux with vigorous stirring. The reaction was carefully monitored until it became clear, about 1.5 h, and then immediately removed from heat. By this time all of the starting material had dissolved but a black tarry residue remained. The solution was decanted and cooled, allowing the product to precipitate. This material was filtered and washed with ethyl ether to remove all traces of phenyl ether. A second crop was obtained by vigorously washing the tarry residue with ethanol (16×250 mL), filtering and evaporating the ethanol, and rinsing the material with ethyl ether. The total yield was 14.9 g as a pale yellow solid, in 61%; mp 285-289° C. (lit.[221] mp 276° C.); $^1$H NMR (DMSO-$d_6$) δ 5.95 (d, 1H, J=7.3), 6.13 (s, 2H), 6.97 (s, 1H), 7.38 (s, 1H), 7.77 (d, 1H, J=7.3); $^{13}$C NMR (DMSO-$d_6$) δ 97.5, 102.1, 102.6, 108.7, 119.4, 122.0, 130.8, 138.7, 145.8, 151.7.

e. 4-Chloro-6,7-methylenedioxyquinoline. 6,7-Methylenedioxy-4-quinolone (5.0 g, 26.5 mmol) was boiled in $POCl_3$ (75 mL) for 45 min and then cooled. Excess phosphoryl chloride was removed under reduced pressure and ice water (100 mL) was added to hydrolyze any residual phosphoryl chloride. The mixture was basified (pH 9) with ammonium hydroxide, and the solid precipitate was filtered. This material was extracted into ethyl ether (8×100 mL), and the ether solution was dried ($MgSO_4$) and evaporated to provide 4.55 g as a white solid, in 83%; mp 127.5-128° C. (lit.[221] mp 129° C.); $^1$H NMR ($CDCl_3$) δ 6.15 (s, 2H), 7.35 (d, 1H, J=4.7), 7.39 (s, 1H), 7.49 (s, 1H), 8.56 (d, 1H, J=4.7); $^{13}$C NMR ($CDCl_3$) δ 99.8, 102.2, 106.1, 119.9, 123.7, 129.8, 141.2, 147.7, 149.1, 151.4.

f. 4-(2-Iodo-4,5-dimethoxybenzyloxy)-6,7-methylenedioxyquinoline. A mixture of 4-Chloro-6,7-methylenedioxyquinoline (414 mg, 2.0 mmol), 2-Iodo-4,5-dimethoxybenzyl alcohol (586 mg, 2.0 mmol), and sodium hydride (252 mg of a 60% dispersion, 6.0 mmol) in DMF (25 mL) was stirred at 105° C. for 90 minutes. The mixture was cooled and a few drops of water were added to quench the excess base. The solvent was evaporated under reduced pressure and the residue was chromatographed in chloroform to give 550 mg as a faintly yellow solid, in 59% yield; mp 196-198° C.; $^1$H NMR (DMSO-d$_6$) δ 3.78 (s, 3H), 3.81 (s, 3H), 5.22 (s, 2H), 6.19 (s, 2H), 7.07 (d, 1H, J=5.4), 7.30 (s, 1H), 7.32 (s, 1H), 7.33 (s, 1H), 7.41 (s, 1H), 8.55 (d, 1H, J=5.4); $^{13}$C NMR (DMSO-d$_6$) δ 56.5, 56.8, 74.4, 89.3, 97.8, 102.2, 102.7, 105.9, 115.4, 116.2, 117.3, 122.8, 131.2, 147.8, 149.8, 149.9, 150.4, 151.2, 160.5; HRMS calcd for $C_{19}H_{16}O_5NI$: 465.0073. Found: 465.0076.

The intermediate 2-Iodo-4,5-dimethoxybenzyl alcohol was prepared as follows.

g. 2-Iodo-4,5-dimethoxybenzyl alcohol. To a stirred mixture of 3,4-dimethyoxybenzyl alcohol (2.0 g, 11.9 mmol) and silver trifluoroacetate (2.82 g, 12.9 mmol) in anhydrous methylene chloride (50 mL) was dropwise added a solution of iodine (3.64 g, 14.1 mmol) in methylene chloride (100 mL). After stirring at ambient temperature for 2 hours, the reaction mixture was filtered and the filtrate was washed with 5% NaHSO$_3$ (2×100 mL) and brine (100 mL), dried (MgSO$_4$) and the solvent was evaporated under vacuum, to provide 3.4 g as a white solid, in 97% yield; $^1$H NMR (CDCl$_3$) δ 3.90 (s, 3H), 3.91 (s, 3H), 4.61 (s, 2H), 6.95 (s, 1H), 7.04 (s, 1H).

EXAMPLE 13

The following illustrate representative pharmaceutical dosage forms, containing a compound of the invention ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |

| -continued | |
|---|---|
| 1.0 N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0-7.5) | q.s. |
| Water for injection | q.s. ad 1 mL |

| (vi) Injection 3 (1 mg/ml) | mg/ml |
|---|---|
| 'Compound X' (free base form) | 1.0 |
| Citric Acid | 0.1% |
| D5W | q.s. ad 1 mL |

| (vii) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

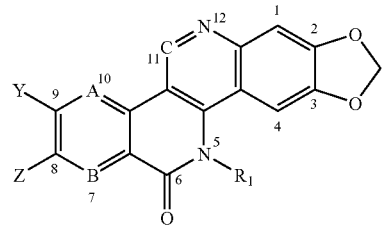

wherein:

A or B is N and the other is CH;

Y and Z are independently hydroxy, $(C_1-C_6)$alkoxy, substituted $(C_1-C_6)$alkoxy, $(C_1-C_6)$alkanoyloxy, substituted $(C_1-C_6)$ alkanoyloxy, —O—P(=O)(OH)$_2$, or —O—C(=O)NR$_c$R$_d$; or Y and Z together with the ring carbon atoms to which they are attached form an alkylenedioxy ring with from 5 to 7 ring atoms;

R$_1$ is $(C_1-C_6)$alkyl; and

R$_c$ and R$_d$ are each independently $(C_1-C_6)$ alkyl or substituted $(C_1-C_6)$ alkyl; or R$_c$ and R$_d$ together with the nitrogen to which they are attached form a N'—(C$_1$-C$_6$)alkylpiperazino, pyrrolidino, or piperidino ring, which ring can optionally be substituted with one or more aryl, heteroaryl, or heterocycle;

or a pharmaceutically acceptable salt thereof.

2. The compound of claim 1 wherein A is N.
3. The compound of claim 1 wherein A is CH.
4. The compound of claim 1 wherein Y is OH.
5. The compound of claim 1 wherein Y is $(C_1\text{-}C_6)$alkoxy.
6. The compound of claim 1 wherein Y is —OCH$_3$.
7. The compound of claim 1 wherein Y is substituted $(C_1\text{-}C_6)$alkoxy.
8. The compound of claim 1 wherein Y is —OCH$_2$CH$_2$OH.
9. The compound of claim 1 wherein Y is —OCH$_2$CH$_2$OCH$_2$CH$_3$.
10. The compound of claim 1 wherein Y is —O—CH$_2$—CHOH—CH$_2$—OH.
11. The compound of claim 1 wherein Y is —O—CH$_2$CH$_2$—NR$_a$R$_b$ wherein R$_a$ and R$_b$ are hydrogen or $(C_1\text{-}C_6)$alkyl.
12. The compound of claim 1 wherein Y is —O—CH$_2$CH$_2$—NR$_a$R$_b$ wherein R$_a$ and R$_b$ together with the nitrogen to which they are attached form a piperazino, pyrrolidino, piperidino, morpholino, or thiomorpholino ring.
13. The compound of claim 1 wherein Y is —O—C(=O)CH$_2$—NR$_a$R$_b$.
14. The compound of claim 1 wherein Y is —O—C(=O)—CHOH—CH$_2$—OH.
15. The compound of claim 1 wherein Y is $(C_1\text{-}C_6)$alkyl substituted with one or more tetrahydrofuranyl, tetrahydropyranyl, or 1,4-dioxanyl rings.
16. The compound of claim 1 wherein Y is —O—C(=O)CH$_2$—NR$_a$R$_b$.
17. The compound of claim 1 wherein Z is OH.
18. The compound of claim 1 wherein Z is $(C_1\text{-}C_6)$alkoxy.
19. The compound of claim 1 wherein Z is OCH$_3$.
20. The compound of claim 1 wherein Z is substituted $(C_1\text{-}C_6)$alkoxy.
21. The compound of claim 1 wherein Z is —OCH$_2$CH$_2$OH.
22. The compound of claim 1 wherein Z is —OCH$_2$CH$_2$OCH$_2$CH$_3$.
23. The compound of claim 1 wherein Z is —O—CH$_2$—CHOH—CH$_2$—OH.
24. The compound of claim 1 wherein Z is —O—CH$_2$CH$_2$—NR$_a$R$_b$ wherein R$_a$ and R$_b$ are hydrogen or $(C_1\text{-}C_6)$alkyl.
25. The compound of claims 1 wherein Z is —O—CH$_2$CH$_2$—NR$_a$R$_b$ wherein R$_a$ and R$_b$ together with the nitrogen to which they are attached form a piperazino, pyrrolidino, piperidino, morpholino, or thiomorpholino ring.
26. The compound of claim 1 wherein Z is —O—C(=O)—CHOH—CH$_2$—OH.
27. The compound of claim 1 wherein Z is $(C_1\text{-}C_6)$alkyl substituted with one or more tetrahydrofuranyl, tetrahydropyranyl, or 1,4-dioxanyl rings.
28. The compound of claim 1 wherein Z is —O—C(=O)CH$_2$—NR$_a$R$_b$.
29. The compound of claim 1 wherein R$_1$ is $(C_1\text{-}C_6)$alkyl.
30. The compound of claim 1 wherein R$_1$ is methyl.
31. The compound of claim 1 wherein R$_1$ is ethyl.
32. The compound of claim 1 wherein R$_1$ is propyl.
33. The compound of claim 1 wherein R$_1$ is isopropyl.
34. The compound of claim 1 wherein R$_1$ is n-butyl.
35. The compound of claim 1 wherein R$_1$ is iso-butyl.
36. The compound of claim 1 wherein R$_1$ is n-pentyl.
37. The compound of claim 1 wherein R$_1$ is isopentyl.
38. The compound of claim 1 wherein R$_1$ is n-hexyl.
39. The compound 12-ethyl-2,3-dimethoxy-12H-8,10-dioxa-6,12-diaza-cyclopenta[b]chrysen-13-one and 12-butyl-2,3-dimethoxy-12H-8,10-dioxa-6,12-diaza-cyclopenta[b]chrysen-13-one, or a pharmaceutically acceptable salt thereof.

40. A compound of formula II:

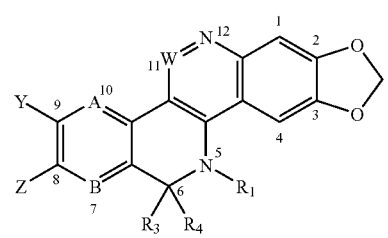

wherein:
A or B is N and the other is CH;
W is CH;
R$_3$ and R$_4$ are both H, or R$_3$ and R$_4$ together are =O, =S, =NH or =N—R$_2$ wherein R$_2$ is $(C_1\text{-}C_6)$alkyl or substituted $(C_1\text{-}C_6)$alkyl;
Y and Z are independently hydroxy, $(C_1\text{-}C_6)$alkoxy, substituted $(C_1\text{-}C_6)$alkoxy, $(C_1\text{-}C_6)$alkanoyloxy, substituted $(C_1\text{-}C_6)$ alkanoyloxy, —O—P(=O)(OH)$_2$, or —O—C(=O)NR$_c$R$_d$; or Y and Z together with the ring carbon atoms to which they are attached form an alkylenedioxy ring with from 5 to 7 ring atoms;
R$_1$ is hydrogen or $(C_1\text{-}C_6)$alkyl; and
R$_c$ and R$_d$ are each independently $(C_1\text{-}C_6)$ alkyl or substituted $(C_1\text{-}C_6)$ alkyl; or R$_c$ and R$_d$ together with the nitrogen to which they are attached form a N'—$(C_1$-$C_6)$alkylpiperazino, pyrrolidino, or piperidino ring, which ring can optionally be substituted with one or more aryl, heteroaryl, or heterocycle;
provided that at least one or both A and B is N; and
provided that when R$_3$ and R$_4$ are both H then W is CH;
or a pharmaceutically acceptable salt thereof.

41. The compound of claim 40 wherein A is N.
42. The compound of claim 40 wherein A is CH.
43. The compound of claim 40 wherein Y is OH.
44. The compound of claim 40 wherein Y is $(C_1\text{-}C_6)$ alkoxy.
45. The compound of claim 40 wherein Y is —OCH$_3$.
46. The compound of claim 40 wherein Y is substituted $(C_1\text{-}C_6)$alkoxy.
47. The compound of claim 40 wherein Y is —OCH$_2$CH$_2$OH.
48. The compound of claim 40 wherein Y is —OCH$_2$CH$_2$OCH$_2$CH$_3$.
49. The compound of claim 40 wherein Y is —O—CH$_2$—CHOH—CH$_2$—OH.
50. The compound of claim 40 wherein Y is —O—CH$_2$CH$_2$—NR$_a$R$_b$ wherein R$_a$ and R$_b$ are hydrogen or $(C_1\text{-}C_6)$alkyl.
51. The compound of claim 40 wherein Y is —O—CH$_2$CH$_2$—NR$_a$R$_b$ wherein R$_a$ and R$_b$ together with the nitrogen to which they are attached form a piperazino, pyrrolidino, piperidino, morpholino, or thiomorpholino ring.
52. The compound of claim 40 wherein Y is —O—C(=O)CH$_2$—NR$_a$R$_b$.
53. The compound of claim 40 wherein Y is —O—C(=O)—CHOH—CH$_2$—OH.
54. The compound of claim 40 wherein Y is $(C_1\text{-}C_6)$alkyl substituted with one or more tetrahydrofuranyl, tetrahydropyranyl, or 1,4-dioxanyl rings.

55. The compound of claim 40 wherein Y is —O—C(=O)CH$_2$—NR$_a$R$_b$.

56. The compound of claim 40 wherein Z is OH.

57. The compound of claim 40 wherein Z is (C$_1$-C$_6$) alkoxy.

58. The compound of claim 40 wherein Z is OCH$_3$.

59. The compound of claim 40 wherein Z is substituted (C$_1$-C$_6$)alkoxy.

60. The compound of claim 40 wherein Z is —OCH$_2$CH$_2$OH.

61. The compound of claim 40 wherein Z is —OCH$_2$CH$_2$OCH$_2$CH$_3$.

62. The compound of claim 40 wherein Z is —O—CH$_2$—CHOH—CH$_2$—OH.

63. The compound of claim 40 wherein Z is —O—CH$_2$CH$_2$—NR$_a$R$_b$ wherein R$_a$ and R$_b$ are hydrogen or (C$_1$-C$_6$)alkyl.

64. The compound of claim 40 wherein Z is —O—CH$_2$CH$_2$—NR$_a$R$_b$ wherein R$_a$ and R$_b$ together with the nitrogen to which they are attached form a piperazino, pyrrolidino, piperidino, morpholino, or thiomorpholino ring.

65. The compound of claim 40 wherein Z is —O—C(=O)—CHOH—CH$_2$—OH.

66. The compound of claim 40 wherein Z is (C$_1$-C$_6$)alkyl substituted with one or more tetrahydrofuranyl, tetrahydropyranyl, or 1,4-dioxanyl rings.

67. The compound of claim 40 wherein Z is —O—C(=O)CH$_2$—NR$_a$R$_b$.

68. The compound of claim 40 wherein R$_3$ and R$_4$ are both H.

69. The compound of claim 40 wherein R$_3$ and R$_4$ together are =O.

70. The compound of claim 40 wherein R$_3$ and R$_4$ together are =S.

71. The compound of claim 40 wherein R$_3$ and R$_4$ together are =NH.

72. The compound of claim 40 wherein R$_3$ and R$_4$ together are =N—R$_2$ where R$_2$ is (C$_1$-C$_6$)alkyl.

73. The compound of claim 40 wherein R$_3$ and R$_4$ together are =N—R$_2$ where R$_2$ is substituted (C$_1$-C$_6$)alkyl.

74. The compound of claim 40 wherein R$_3$ and R$_4$ together are =N—R$_2$ where R$_2$ is a (C$_1$-C$_6$)alkyl substituted with one or more hydroxy, mercapto, carboxy, amino, piperazinyl, pyrrolidinyl, piperidinyl, morpholinyl, thiomorpholinyl, tetrahydrofuranyl, tetrahydropyranyl, or 1,4-dioxanyl groups.

75. The compound of claim 40 wherein R$_3$ and R$_4$ together are =N—R$_2$ where R$_2$ has from 2 to 4 carbon atoms and substituted with one to two groups selected from hydroxy, mercapto, carboxy, amino, piperazinyl, pyrrolidinyl, piperidinyl, morpholinyl, thiomorpholinyl, tetrahydrofuranyl, tetrahydropyranyl, or 1,4-dioxanyl.

76. The compound of claim 40 wherein R$_3$ and R$_4$ together are =N—R$_2$ where R$_2$ is —CH$_2$CH$_2$—NR$_a$R$_b$ wherein R$_a$ and R$_b$ are hydrogen or (C$_1$-C$_6$)alkyl.

77. The compound of claim 40 wherein R$_3$ and R$_4$ together are =N—R$_2$ where R$_2$ is —CH$_2$CH2-NR$_a$R$_b$ wherein R$_a$ and R$_b$ together with the nitrogen to which they are attached form a piperazino, pyrrolidino, piperidino, morpholino, or thiomorpholino ring.

78. The compound of claim 40 wherein R$_1$ is hydrogen.

79. The compound of claim 40 wherein R$_1$ is (C$_1$-C$_6$) alkyl.

80. The compound of claim 40 wherein R$_1$ is isobutyl.

81. The compound of claim 40 wherein R$_1$ is n-butyl.

82. The compound of claim 40 wherein R$_1$ is isopentyl.

83. The compound 12-butyl-2,3-dimethoxy-12H-8,10-dioxa-4,5,6,12-tetraaza-cyclopenta[b]chrysen-13-one; 12-butyl-2,3-dimethoxy-12H-8,10-dioxa-1,5,6,12-tetraaza-cyclopenta[b]chrysen-13-one; 12-butyl-2,3-dimethoxy-12H-8,10-dioxa-1,4,5,6,12-pentaaza-cyclopenta[b]chrysen-13-one; or a pharmaceutically acceptable salt thereof.

84. A pharmaceutical composition comprising a compound as described in claim 1, or 40 in combination with a pharmaceutically acceptable diluent or carrier.

85. A method of inhibiting breast cancer cell growth, comprising administering to a mammal afflicted breast with cancer, an amount of a compound as described in claim 1, or 40 effective to inhibit the growth of said breast cancer cells.

86. A method comprising inhibiting breast cancer cell growth by contacting said breast cancer cell in vitro or in vivo with an amount of a compound as described in claim 1, or 40 effective to inhibit the growth of said breast cancer cell.

* * * * *

UNITED STATES PATENT AND TRADEMARK OFFICE
CERTIFICATE OF CORRECTION

| | |
|---|---|
| PATENT NO. | : 7,319,105 B2 |
| APPLICATION NO. | : 10/846936 |
| DATED | : January 15, 2008 |
| INVENTOR(S) | : Edmond J. LaVoie et al. |

It is certified that error appears in the above-identified patent and that said Letters Patent is hereby corrected as shown below:

In column 66, line 14, claim 77, delete "—$CH_2C$ H2" and insert -- -$CH_2CH_2$--, therefor.

In column 66, line 34, claim 85, delete "breast with" and insert --with breast--, therefor.

Signed and Sealed this

Twenty-seventh Day of May, 2008

JON W. DUDAS
*Director of the United States Patent and Trademark Office*